United States Patent
Kim et al.

(10) Patent No.: US 12,161,822 B2
(45) Date of Patent: Dec. 10, 2024

(54) INTRODUCTION DEVICE INCLUDING AN ELECTROACTIVE TIP ON A GUIDEWIRE

(71) Applicants: XCATH, INC., Houston, TX (US); THE BOARD OF REGENTS OF THE UNIVERSITY OF TEXAS SYSTEM, Austin, TX (US)

(72) Inventors: Daniel H. Kim, Houston, TX (US); Dong Suk Shin, Houston, TX (US); Viljar Palmre, Pearland, TX (US); Younghee Shim, Houston, TX (US); Bhavik Patel, Houston, TX (US)

(73) Assignees: BOARD OF REGENTS OF THE UNIVERSITY OF TEXAS SYSTEM, Austin, TX (US); XCATH, INC., Houston, TX (US)

( * ) Notice: Subject to any disclaimer, the term of this patent is extended or adjusted under 35 U.S.C. 154(b) by 1046 days.

(21) Appl. No.: 17/051,311

(22) PCT Filed: Apr. 25, 2019

(86) PCT No.: PCT/US2019/029196
§ 371 (c)(1),
(2) Date: Oct. 28, 2020

(87) PCT Pub. No.: WO2019/212863
PCT Pub. Date: Nov. 7, 2019

(65) Prior Publication Data
US 2021/0060310 A1   Mar. 4, 2021

Related U.S. Application Data

(60) Provisional application No. 62/664,753, filed on Apr. 30, 2018.

(51) Int. Cl.
*A61M 25/09* (2006.01)
*A61M 25/01* (2006.01)

(52) U.S. Cl.
CPC ........ *A61M 25/09* (2013.01); *A61M 25/0158* (2013.01); *A61M 2025/09083* (2013.01);
(Continued)

(58) Field of Classification Search
CPC .............. A61M 25/09; A61M 25/0158; A61M 2025/0983; A61M 2025/0915; A61M 2025/09175; A61M 2205/0283
See application file for complete search history.

(56) References Cited

U.S. PATENT DOCUMENTS

| | | | | |
|---|---|---|---|---|
| 4,944,727 A | * | 7/1990 | McCoy | A61M 25/0158 604/528 |
| 5,178,159 A | * | 1/1993 | Christian | A61B 8/06 600/585 |

(Continued)

FOREIGN PATENT DOCUMENTS

| | | |
|---|---|---|
| JP | H02199781 A | 8/1990 |
| JP | H05212119 A | 8/1993 |

(Continued)

OTHER PUBLICATIONS

Japanese Application No. 2020-512455, Office Action dated Mar. 16, 2021, 12 pages.

(Continued)

*Primary Examiner* — Devin B Henson
(74) *Attorney, Agent, or Firm* — Patterson + Sheridan, LLP

(57) ABSTRACT

A catheter comprises a hollow sheath, a guidewire extendable through the hollow sheath, where the guidewire comprises a controllably bendable tip portion, a hollow tubular intermediate portion connected to the tip portion, an electrical connection portion connected to the hollow tubular portion, at least a first wire extending through the hollow tubular portion and connected at a first end thereof to a first (Continued)

circumferential conductor and at a second end thereof to a surface of the tip end, and a power supply connector, therein the electrical connection portion is received in the power supply connector and a first terminal in the power supply connector contacts the first circumferential conductor.

20 Claims, 28 Drawing Sheets

(52) U.S. Cl.
CPC .............. *A61M 2025/0915* (2013.01); *A61M 2025/09175* (2013.01); *A61M 2205/0283* (2013.01)

(56) References Cited

U.S. PATENT DOCUMENTS

| | | | |
|---|---|---|---|
| 5,238,005 | A | 8/1993 | Iran et al. |
| 5,517,989 | A * | 5/1996 | Frisbie .................. A61N 1/40 606/41 |
| 9,364,640 | B2 * | 6/2016 | Vanney .................. A61B 5/066 |
| 2004/0064172 | A1 | 4/2004 | McVenes et al. |
| 2004/0230271 | A1 | 11/2004 | Wang et al. |
| 2007/0106165 | A1 | 5/2007 | Tulkki |
| 2013/0053865 | A1 | 2/2013 | Bridgeman et al. |
| 2013/0123692 | A1 * | 5/2013 | Zhang .................. A61M 25/09 604/95.05 |
| 2016/0074630 | A1 | 3/2016 | Murata et al. |
| 2016/0271365 | A1 | 9/2016 | Forber et al. |
| 2017/0303856 | A1 | 10/2017 | Toth et al. |

FOREIGN PATENT DOCUMENTS

| | | |
|---|---|---|
| JP | H8-10336 | 1/1996 |
| JP | 2006334198 A | 12/2006 |
| JP | 2015-80500 A | 4/2015 |
| JP | 2016-518943 A | 6/2016 |
| WO | 2017-136729 A1 | 8/2017 |

OTHER PUBLICATIONS

PCT International Search Report and Written Opinion for PCT/US2019/019296, mailed Aug. 21, 2019.
Japanese Application No. 2020-512455, Office Action dated Jun. 13, 2023, 6 pages.
Korean Application No. 10-2022-7028470, Decision for Grant dated May 3, 2023, 4 pages.
European Patent Application No. 17795762.4, Communication dated Apr. 4, 2023, 5 pages.
Chinese Application No. 202111506221.2, Office Action dated Nov. 14, 2023, 16 pages.
Japanese Application No. 2020-512455, Office Action dated Jul. 26, 2022, 3 pages.
Japanese Application No. 2020-512455, Office Action dated Nov. 24, 2021, 10 pages.
Korean Application No. 10-2020-7005805, Office Action dated Oct. 29, 2021, 14 pages.
Korean Application No. 10-2022-7028470, Office Action dated Oct. 31, 2022, 6 pages.
Korean Application No. 10-2022-7028471, Office Action dated Nov. 30, 2022, 6 pages.
Chinese Patent Application No. 201980004191.X, Office Action dated Feb. 24, 2022 with English translation, 19 pages.
Canadian Patent Application No. 3,073,748, Office Action dated Apr. 8, 2021, 3 pages.
European Patent Application No. 19795762.4, Extended Search Report dated May 11, 2021, 5 pages.
Chinese Patent Application No. 201980004191.X, Office Action dated Jul. 29, 2021 with English translation, 21 pages.
Mexican Patent Application No. MX/a/2020/002362 Office Action dated Jul. 5, 2023, 4 pages.
Japanese Patent Application No. 2022-185527, Office Action dated Sep. 26, 2023, 13 pages.

* cited by examiner

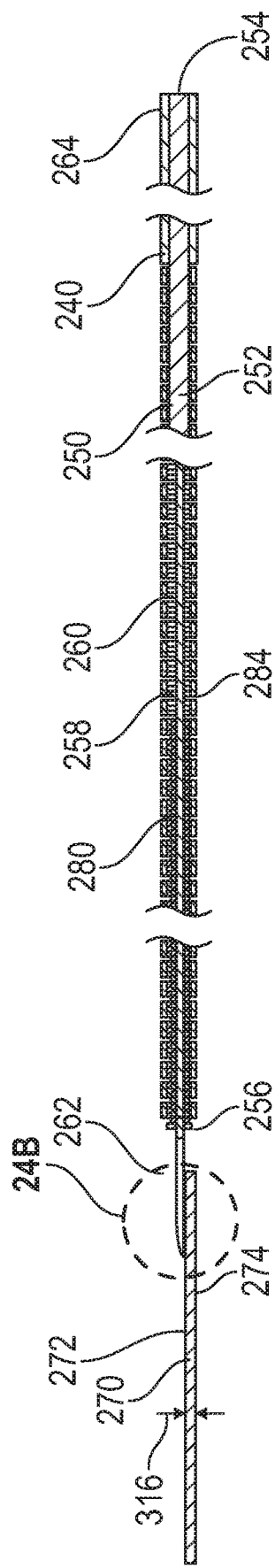
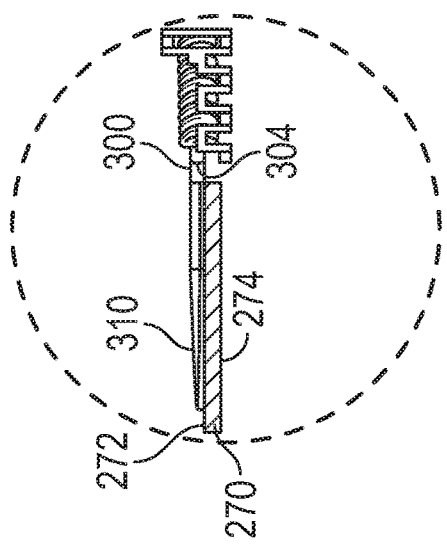
FIGURE 24A
FIGURE 24B

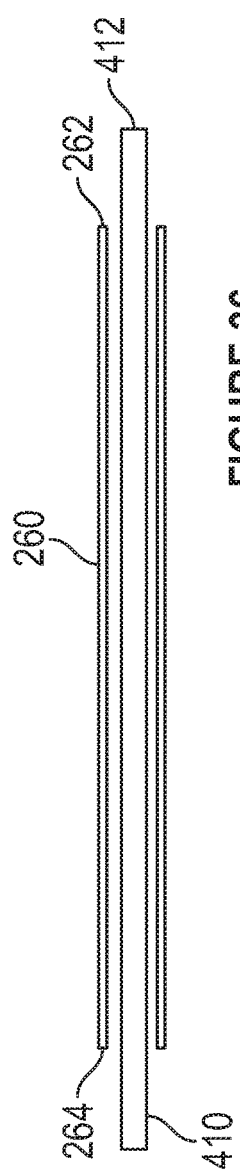
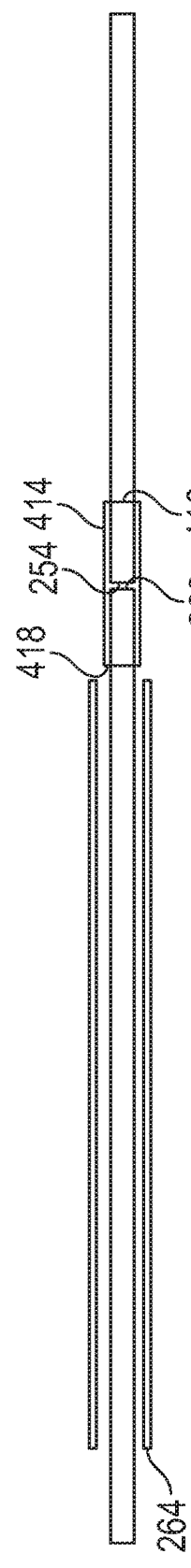
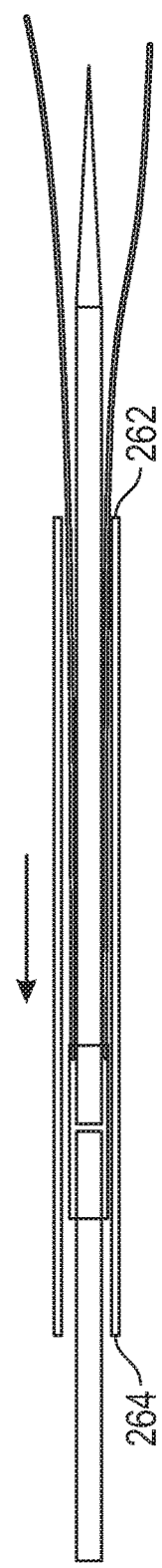
FIGURE 36
FIGURE 37
FIGURE 38

INTRODUCTION DEVICE INCLUDING AN ELECTROACTIVE TIP ON A GUIDEWIRE

CROSS-REFERENCE TO RELATED APPLICATION

This application for Patent is a national stage application under 35 U.S.C. 371 of PCT/US2019/029196, filed Apr. 25, 2019, which claims benefit of U.S. Provisional Application No. 62/664,753, filed Apr. 30, 2018, entitled "INTRODUCTION DEVICE INCLUDING AN ELECTROACTIVE TIP ON A GUIDEWIRE," which is are both incorporated herein by reference in their entireties.

BACKGROUND

Field

The present disclosure relates to the field of intraluminal guidewires and catheters, more particularly to the field of guidewires and catheters employing an electroactive polymer tip end.

Description of the Related Art

Guidewires are used to guide a secondary sheath, which is fed along and over the guidewire, to a desired location in a body, for example a mammalian body such as a human body. In one application, a guidewire is introduced into a body lumen, i.e., a blood vessel, through an incision through the patient's skin and the lumen wall, and the introduced, or distal, end of the guidewire is guided therefrom to a desired location of the lumen, or of a lumen which branches into, or from, the lumen into which the guidewire is introduced.

One issue with guidewire introduction systems is the limited ability to conform the distal end of the guidewire to follow tortuous lumen geometries, as well as to guide the distal end into an intersecting lumen or branch lumen to the lumen within which the distal end of the guidewire is positioned. To guide the distal end of the guidewire into a branch lumen, the distal end of the guidewire must be controllably moved from alignment with the lumen in which it reached the branching lumen location to an alignment whereby further movement of the guidewire inwardly of the body will cause the guidewire to enter and follow the branch lumen. In some cases, the branch lumen, a location of which is the target destination of the distal end of the guidewire, intersects the lumen in which the distal end is present at a large angle, for example greater than forty-five, degrees, and in some cases greater than ninety degrees.

One methodology for controlling the orientation of the distal end of the guidewire includes incorporating an electroactive polymer contacted by at least two electrical conductors located at at least two different locations on the electroactive polymer. By selectively biasing at least one of the electrical conductors, the orientation of the electroactive polymer portion of the guidewire is controllably changeable with respect to the remainder of the guidewire. When the bias is removed, the section of the guidewire having the electroactive polymer therein returns to its free state. By locating the electroactive polymer section of the guidewire at, or as, the distal end of the guidewire. The location of the distal tip of the guidewire can be controllably positioned by a user of the guidewire.

Present guidewire systems suffer from several reliability and functional limitations due to their construction. The range of motion of the distal end of the electroactive polymer section has an inherent limited physical range, which limits the ability to position the distal end of the guidewire into intersecting lumens at a high angle of incidence with the lumen in which the guidewire is being currently guided. Additionally, as the conductors used to actuate the electroactive polymer section must be connected to at least one of an electrical bias voltage or electrical ground to establish a bias across the electroactive polymer, the electroactive polymer portion of the guidewire is hard-wired to a voltage source and a ground, and the rotational actuation of the guidewire by the user is resultantly limited.

Additionally, the guidewire geometries are very small, composing rods or tubes having a diameter on the order of one to four mm. The conductors to provide the bias across the electroactive polymer section must extend along, or within, the guidewire, and the connections thereof with the surface of the electroactive polymer, or with electrodes contacting the surface of the electroactive polymer, are small and fragile, leading to frequent open circuit situations where the distal end of the guidewire cannot be remotely manipulated by the user.

SUMMARY

Herein, there are provided a guidewire system incorporating an electroactive polymer section, wherein the range of positioning of the distal tip of the guidewire, with respect to the main body of the guidewire, is actuable through angles greater than ninety degrees, such as that disclosed in WO 2017136729 A1 and U.S. Provisional Application No. 62/539,346 incorporated herein by reference. Additionally, the guidewire system is configured for infinite rotation while maintaining a conductive electrical path between a voltage source, electrical ground, or both, to the wall or side of the electroactive polymer from a location exterior to the body into which the guidewire is to be introduced, such as on, or adjacent to, the proximal end of the guidewire. Further, an improved connection paradigm between the electrical conductors and the electroactive polymer is provided.

In one aspect, the catheter comprises a hollow sheath, a guidewire extendable through the hollow sheath, where the guidewire comprises a controllably bendable tip portion, a hollow tubular intermediate portion connected to the tip portion, an electrical connection portion connected to the hollow tubular portion, at least a first wire extending through the hollow tubular portion and connected at a first end thereof to a first circumferential conductor and at a second end thereof to a surface of the tip end, and a power supply connector, wherein the electrical connection portion is received in the power supply connector and a first terminal in the power supply connector contacts the first circumferential conductor.

In another aspect, the catheter includes a controllably bendable distal portion, a hollow tubular intermediate portion connected to the distal portion, a proximal electrical connection portion connected to the hollow tubular portion, at least a core extending through the hollow tubular portion and connected at a proximal end thereof to a proximal electrical connection portion and at a distal end thereof to a surface of a tip end of the distal portion, and a power supply connector, therein the electrical connection portion is received in the power supply connector and a first terminal in the power supply connector contacts the proximal electrical connection portion.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 24A is a sectional view of the catheter of FIG. 18, and FIG. 24B is an enlarged view of the catheter of FIG. 18 showing the connection of the lead to the electroactive polymer portion;

FIG. 36 is a schematic view of a step in the assembly of the guidewire of FIG. 35;

FIG. 37 is a schematic view of a further step in the assembly of the guidewire of FIG. 35;

FIG. 38 is a schematic view of a yet further step in the assembly of the guidewire of FIG. 35;

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
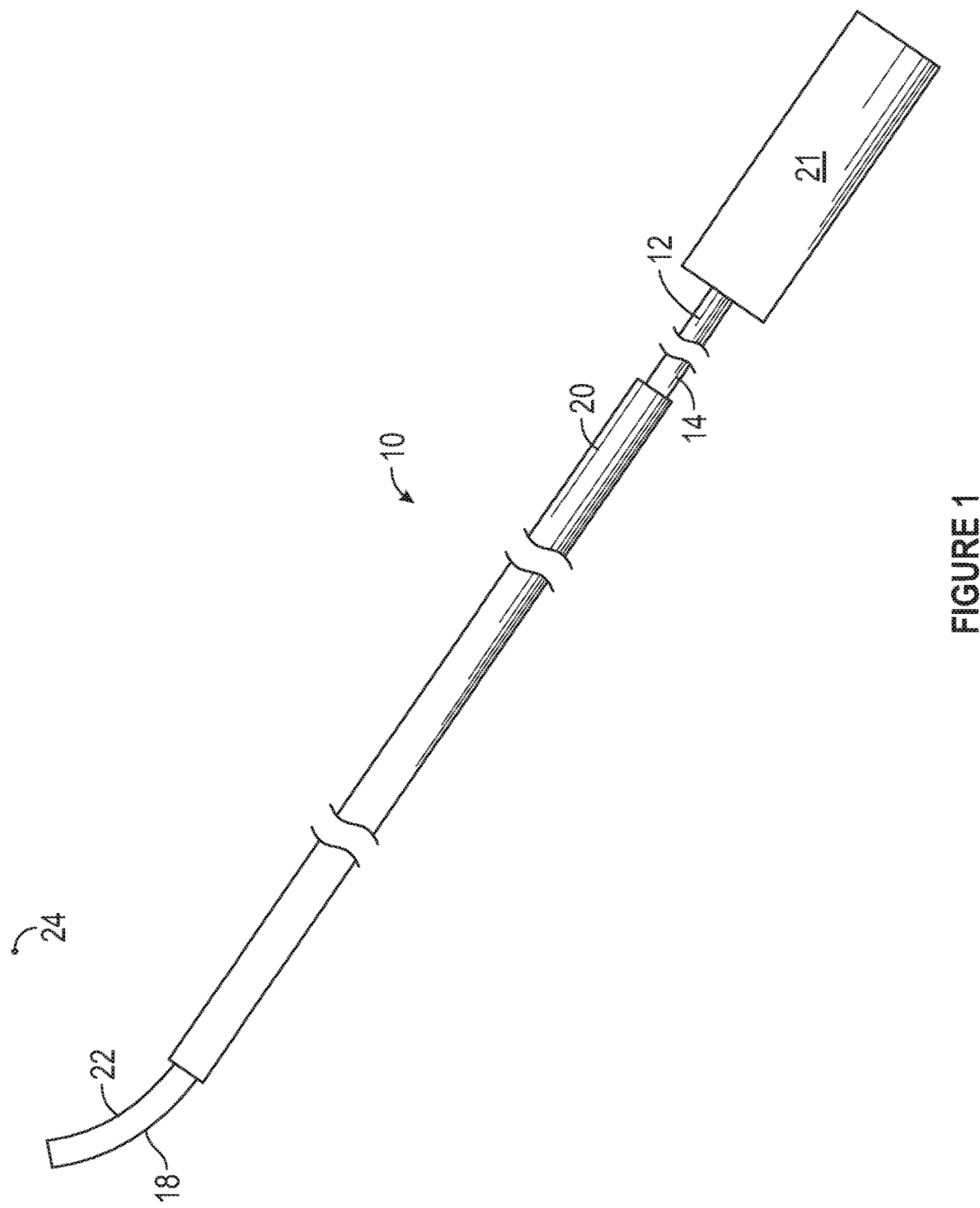
FIG. 1 is a schematic plan view of a catheter including an outer sheath, and inner guidewire, and an electrical connection.
Figure 2:
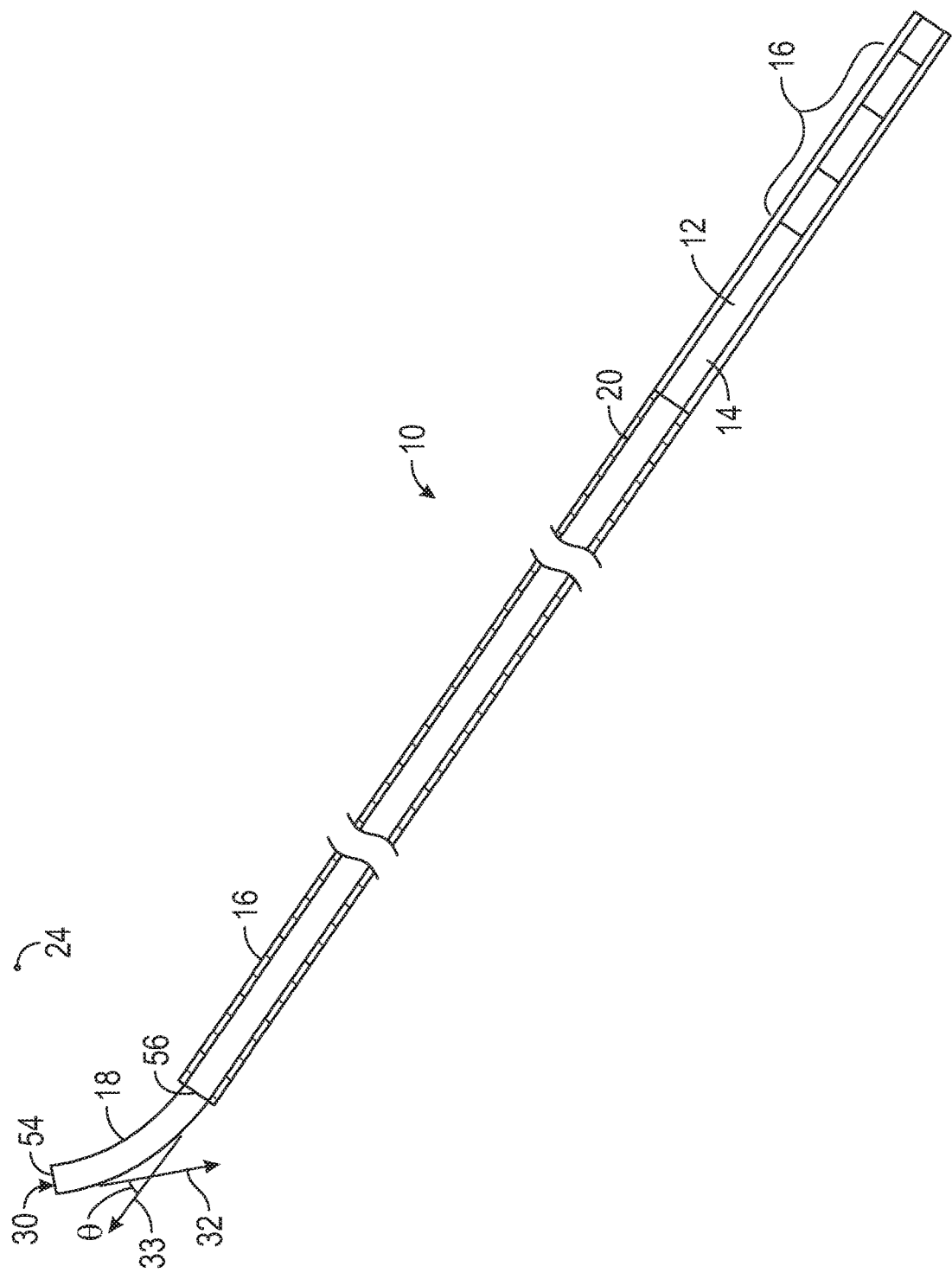
FIG. 2 is a schematic sectional view of the catheter of FIG. 1.

Referring initially to FIGS. 1 and 2, there is shown a guidewire system 10 in FIG. 1, including a guidewire 12 fully shown in FIG. 2, a sheath 20 surrounding a majority of the length of the guidewire 12, and a power supply connector 21 disposable over the proximal end of the guidewire 12. The guidewire 12 is composed of a hollow, tubular shaft 14 forming the intermediate portion thereof, an electrical connection portion 16 (FIGS. 2 and 16) forming the proximal end thereof, and a controllably bendable portion 18 forming the distal end of the guidewire 12. Here, the guidewire 12 is shown extended in a generally straight line path, and, the bendable portion 18 in its free state, i.e. without an electrical bias applied thereacross, is shown having a curve or bend 22 therein. The bend 22 is shown in FIG. 2 as a continuous curve having a radius centered about point 24, and may be formed by pressing the controllably bendable portion over a round or curved mandrill to conform the controllably bendable portion to the curved surface thereof. Alternatively, the bend 22 forming a pre-bent portion of the controllably bendable portion 18 may be formed along only a small length of, in other words over only a portion of the length of, the controllably bendable portion 18, such that generally straight sections of the controllably bendable portion 18 extend from one, or both sides, of the bend. Other bends, such as compound bends including two or more bend angles along the length of the controllably bendable portion 18 are also contemplated.

Figure 3:
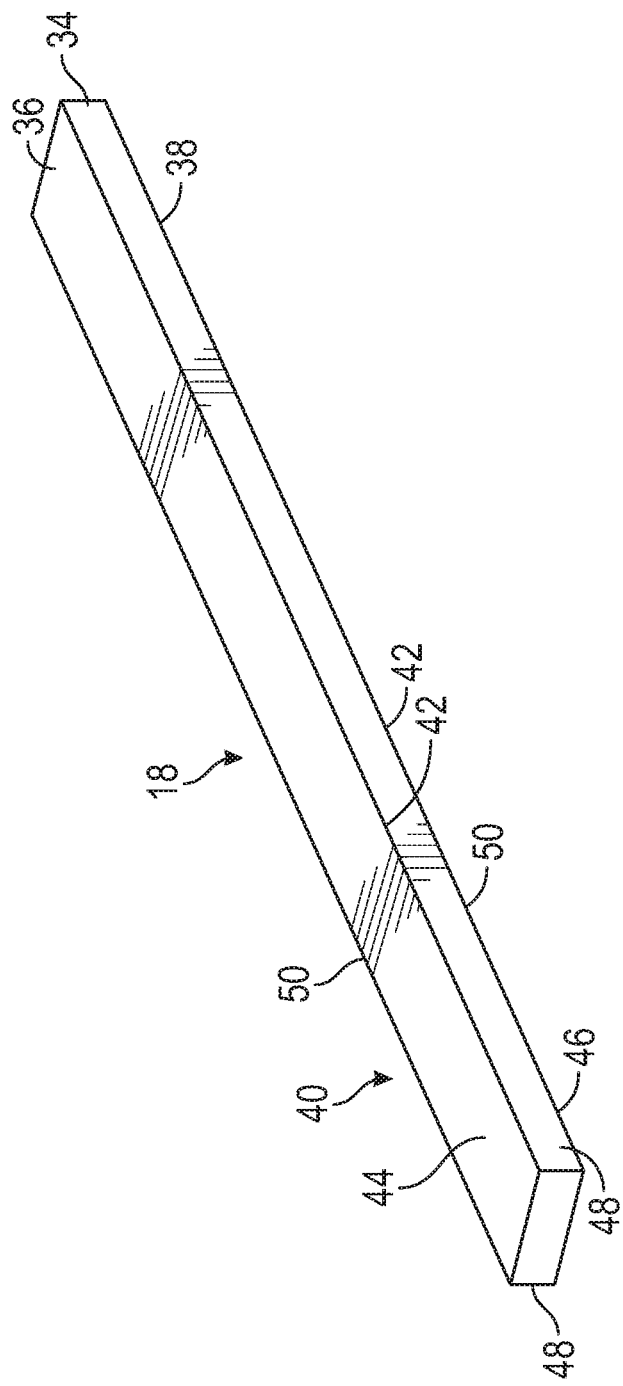
FIG. 3 is an isometric view of a controllably bendable tip of the catheter of FIGS. 1 and 2.

As shown in FIG. 3, in one aspect, the controllably bendable portion 18 is configured from an electroactive polymer portion 34 sandwiched between electrodes 36, 38 directly formed on, or bonded to, opposed sides of the electroactive polymer portion 34.

By forming the controllably bendable portion 18 as including a deviation from a straight line path in its free state, such as by providing a bend or curve therein in the free, or un-energized, state thereof, the orientation of a tangent 32 to the tip 30 end of the controllably bendable portion 18 can be disposed at an angle θ of between about 0 to about 90 degrees from a tangent 33 to the controllably bendable portion 18 at the connection location therewith to the hollow, tubular, shaft 14 as shown in FIG. 2. It is contemplated herein that a tangent 32 to the tip 30 end of the controllably bendable portion 18 can be disposed at an angle greater than 90 degrees from a tangent to the connection location thereof with the hollow, tubular, shaft 14, or an additional intermediate member therebetween. For example, if the tip 30 end of the controllably bendable portion is, in its free state, oriented 45 degrees from the orientation of the end of the hollow, tubular, shaft 14, and the tip 30 end of the controllably bendable portion 18 can be bent through an angle of +/−45 degrees by electrical actuation of the electrically actuable polymer thereof, the tip 30 end can, under control of an operator, be oriented from 0 to 90 degrees with respect to the connection location of the controllably bendable section 18 to the hollow, tubular, shaft 14, i.e., the range of the angle θ is between about 0 to about 90 degrees. If the controllably bendable portion 18 can be controllably actuated between +/−60 degrees with the same pre-bend conditions thereof, then the angle θ can be controllably established at between −15 and +105 degrees. By selecting the pre-bend angle and the bendability of the controllably bendable portion, the operator or user of the guidewire system 10 can controllably select a desired orientation of the tip 30 end with respect to the hollow tubular shaft 14 to allow locating of the tip 30 end of the guidewire 12 to establish positioning thereof in tortuous lumen anatomy, including into branch lumens.

Herein, in one aspect the controllably bendable portion 18 is configured having an electroactive polymer base in strip form, having opposed electric conductors on opposed sides of the strip. For example, as shown in FIG. 3, the strip 40 of electroactive polymer portion 34 includes opposed major faces 44, 46, and opposed minor faces 48 wherein each minor face 48 spans between two major faces 44, 46. The major faces 44, 46 are shown as having a rectangular profile, although other profiles, in plain view, such as triangular, a truncated triangular polygon, or other polygon or curved sides shapes are contemplated. On each major face 46, 48 is provided a carbon layer 42 which is pressed and adhered to the electroactive polymer portion 34 by pressing it there against, and an overlying metal electrode 50 over the carbon layer 42. By forming one of the carbon layers 42 on one of the major faces 44 or 46 to be thicker than the one on the other major face 44 or 46, the inherent different stresses in the carbon layers 42 causes the controllably bendable portion 18 to inherently form a continuous curve along its length as shown in FIGS. 1 and 2. The relative thicknesses of the carbon layers 42 dictates the total angular difference (angle θ) between a tangent 32 to the distal end 54 of the controllably bendable portion 18 and a tangent 33 to the proximal end 56 of the controllably bendable portion 18. By maintaining a constant thickness of each of the carbon layers 42 of different thicknesses over their length from the proximal end 56 to the distal end 54 or tip end 30 of the controllably bendable portion 18, the continuous curve will be inherently formed as a result of a constant difference in the internal stress of the two carbon layers 42 over their length from the proximal end 56 to the distal end 54 of the controllably bendable portion 18 centered about point 24. Each metal electrode 50 is provided over a carbon layer 42 to form a highly electrically conductive path to distribute electricity over the length and width of each major face 44, 46, and thereby maintain a uniform voltage potential across the respective electrodes 50. For example, the electrodes 50 may be formed of a sputtered or vapor deposited layer of gold, silver, palladium or platinum, wherein each electrode has the same, or nearly the same, thickness. The carbon layer 42 may comprise carbon-based materials such as carbide-derived carbon, carbon nanotube, graphene, a composite of carbide-derived carbon and polymer electrolyte member, and a composite of carbon nanotube and polymer electrolyte member.

Alternatively, the electrodes 50 themselves may be formed of a shape memory material, for example a NiTi alloy or a NiTi based alloy, formed on the controllably bendable portion 18 by sputtering, vapor deposition or other deposition or adhering methods. In this aspect, for example, a thin layer of a NiTi alloy, formed by co-sputtering of a nickel and a titanium target in a process chamber, is deposited on the major faces 44, 46 of the controllably bendable portion 18. Thereafter, the desired bend or bends are imposed on the controllably bendable portion, for example a continuous curvature, or a sharp kink type bend. Then, the controllably bendable portion 18 is cooled to temperature sufficient to cause a change in the internal phase of the alloy, changing the internal phase structure from austenite to martensite, and the controllably bendable portion 18 is returned to a straight line or nearly straight line configuration as shown in FIG. 3, such that it can be inserted into a delivery sheath or other sheath, and allowed to heat back to a temperature where the internal phases changes back to austenite phase while the controllably bendable portion 18 is still within the sheath 20. The shape memory material can also be deposited onto a pre-bent controllably bendable portion 18.

The shape alloy memory material here also acts as the electrode material. When the distal end of the sheath is inserted into a body lumen or other body region, once the controllably bendable portion is pushed outwardly of the distal end of the sheath, it will revert to the bent shape thereof before it was cooled and bent back into a flat or straight line profile, if no bias or potential is applied across the electroactive polymer. Thus, by applying a bias or potential across the electroactive polymer, the profile of the controllable bendable portion 18 can be changed.

Figure 4:
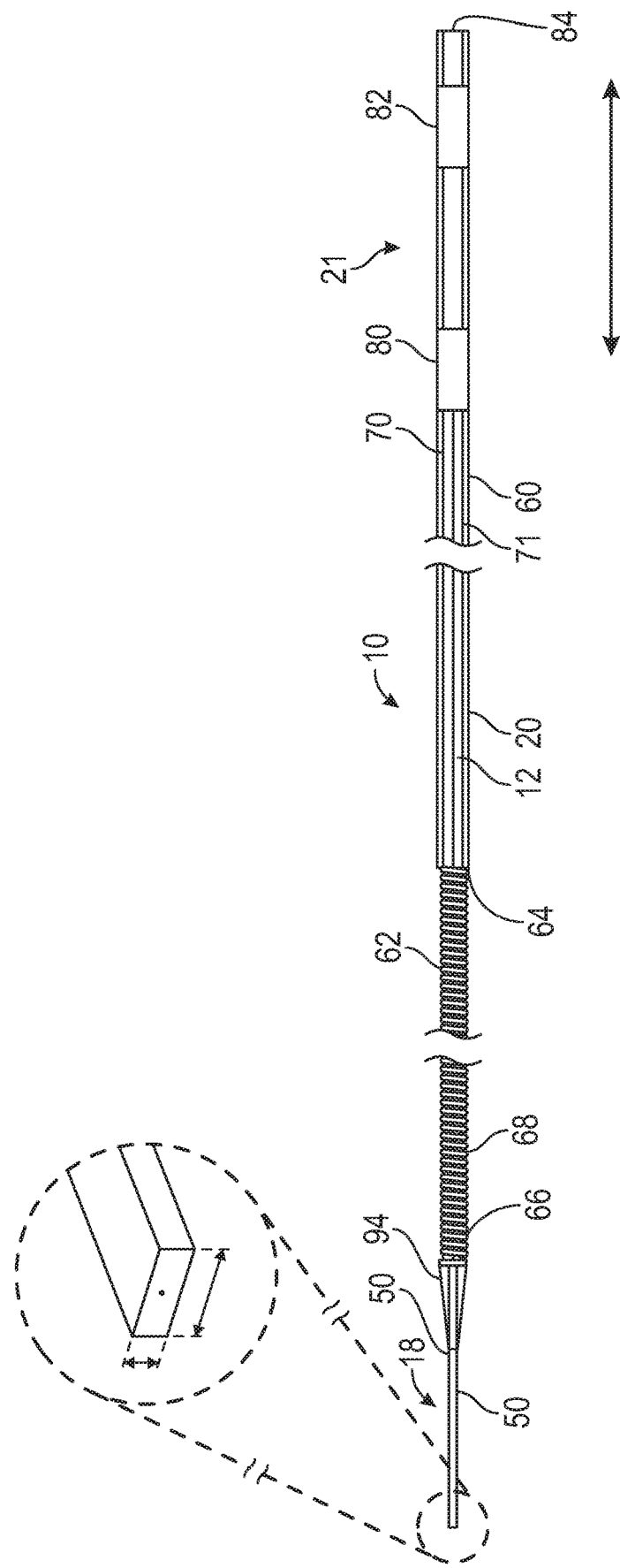
FIG. 4 is a side view of the guidewire of FIGS. 1 and 2.
Figure 5:
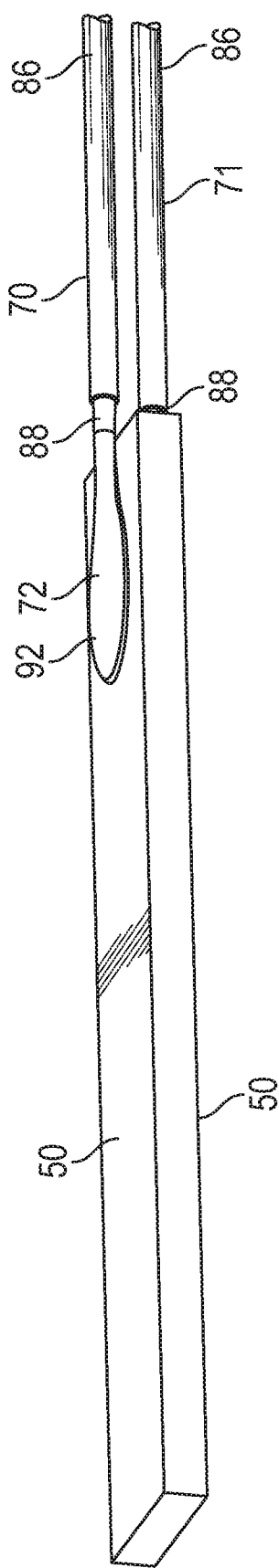
FIG. 5 is a partial view of the guidewire of FIG. 4, showing the interconnection of electrically conductive wires to the controllably bendable tip end thereof.

Referring now to FIGS. 4 and 5, a connection paradigm for connecting the + and − terminals of a power source such as a capacitor or a battery to the opposed electrodes 50 is shown. Here, the guidewire system 10 includes the a guidewire 12, the sheath 20 surrounding a majority of the length of the guidewire 12, and the power supply connector 21 located at the proximal end of the guidewire system as shown in FIG. 1. The guidewire 12 is configured as shown in FIG. 4, to include a first generally tubular portion 60, the controllably bendable portion 18, and a compliant member 62 disposed between, and interconnecting, the distal end 64 of the first tubular portion 60 and the proximal end 66 of the controllably bendable portion 18. Here, the compliant member 62 is configured as a coil spring having windings 68 spaced along the length thereof between the tubular first portion 60 and the controllably bendable portion 18 at an approximately equal pitch. The compliant member 62 provides a compliant support which can follow the tortuous anatomy of a body lumen as the guidewire assembly 10 is guided inwardly of the lumen. Additionally, to connect the opposed electrodes 50 to a power supply, a first wire 70 (FIG. 5) is connected to, and extends between, one of the electrodes 50 and a first terminal 72 located on the outer surface of the generally tubular portion 60, and a second wire 71 (FIG. 5) is connected to, and extends between, the other one of the electrodes 50 and a second terminal 73 located on the outer surface of the generally tubular portion 60 closer to the proximal end 84 of the generally tubular portion 60 than is the first terminal 72.

Figure 6:
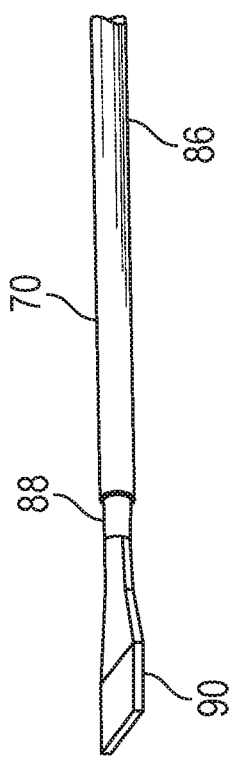
FIG. 6 is an end view of the wire of FIG. 6 before connection thereof to the controllably bendable tip end.
Figure 7:
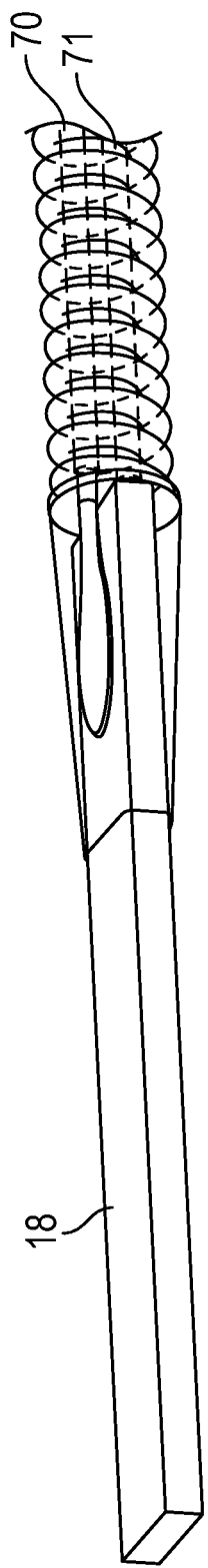
FIG. 7 is an enlarged isometric view of the connection of the controllably bendable tip end to an intermediate portion of the guidewire.
Figure 8:
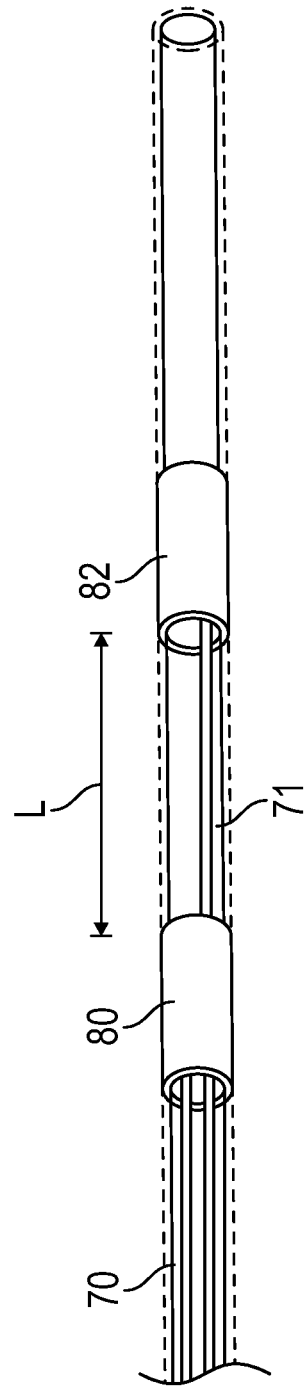
FIG. 8 is an enlarged isometric view of the electrical connection portion of the guidewire.

Referring to FIGS. 5 and 6, each of the wires 70, 71 includes an outer insulative coating 86, and an internal conductive core 88 terminating in a generally flat trapezoidal portion 90 forming the terminals. One of each of the wires 70, 71 are connected to one of the electrodes 50 on the controllably bendable portion with a conductive adhesive 92 (such as a gold paste), thereby providing an electric flow connection between the wires 70, 71 and the terminals 90. As shown in FIGS. 7 and 8, once the terminals 90 are attached to the electrodes 50 on either side of the electroactive polymer in the controllably bendable portion 18, the electroactive polymer is further coated with Polydimethylsiloxane (PDMS) and Parylene and the opposed end of the wires 70, 71 are threaded through the compliant member 62 and connected to one of the terminals 80, 82 to be received in the power supply connector 21, such as by using a conductive adhesive to attach each of the conductive cores 88 of the wires 70, 72 to respective ones of the terminals 80, 82. This can be accomplished by providing a hole through the terminals 80, 82 and bringing the conductive cores 88 inwardly and through the hole from within the tubular envelope of the terminals 80, 82, or other mechanisms. The terminals 80, 82 circumscribe the circumference of the tubular portion 60, and are spaced from one another in the length direction L of the tubular portion 60. As shown in FIG. 4, the proximal end of the controllably bendable portion 18 is adhered to the distal end of the compliant member 62 with an adhesive 94 (e.g. polyimide or UV curing agents), which also covers the conductive adhesive 92.

Figure 9:
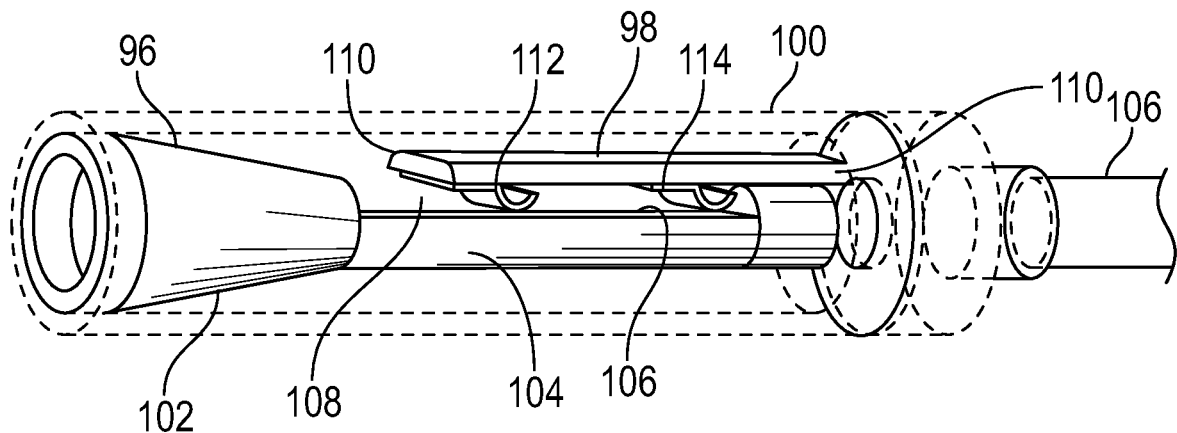
FIG. 9 is a phantom isometric view of the power supply connector for powering the controllably bendable portion of the guidewire of FIG. 4.
Figure 10:
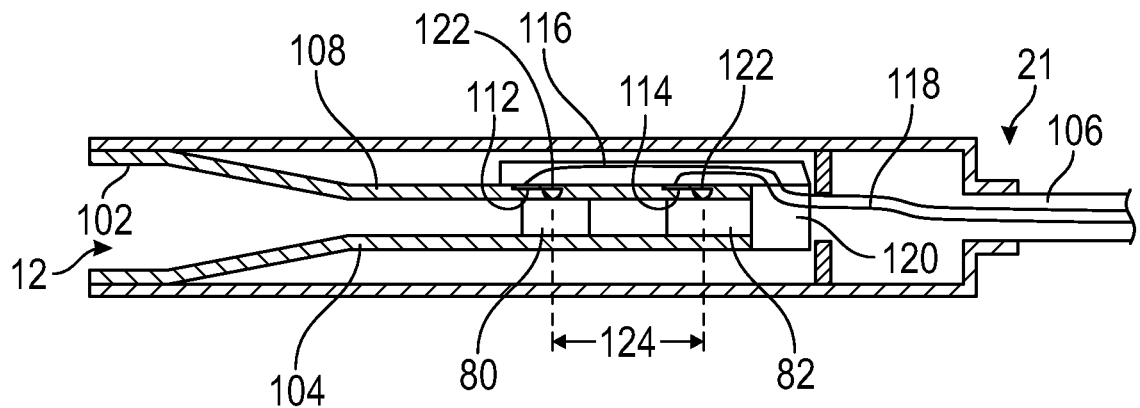
FIG. 10 is a sectional view of the power supply connector of FIG. 9.

Referring now to FIGS. 9 and 10, a connection paradigm of the power supply connector 21 to the controllably bendable portion 18 of the guidewire 12 is shown. Here, the power supply connector 21 includes an outer, generally right annular, housing 100 and an insert 96 received therein, configured of a tapered inlet bore 102 leading to a conduit 104 having a slot opening 108 along the length thereof, and a cantilevered portion 98 extending over, and spaced from, the slot opening 108. The largest outer dimeter of the tapered inlet bore 102 is slightly larger than the inner diameter of the housing 100, and the sidewalls 110 of the cantilevered portion 98 are curved to mimic the curvature of the inner diameter of the housing 100, thus allowing the insert 96 to be pressed into the housing 100 and centering of the insert 96 in the housing 100. On the side surface of the cantilevered portion 98 facing the slot opening 108 are provided a first terminal 112 and a second terminal 114 spaced, and electrically isolated, from one another. The conduit 104 is sized to allow the proximal end of the guidewire 12 to enter thereinto, and allow rotation of the housing 100 and guidewire 12 with respect to one another. Here, the power supply is connected, through a cable 106, to a dc electricity source, for example the output of a variable output, user controllable, AC to DC converter connected to a source of ac power. The cable 106 includes two wires 116, 118, extending therein, and one of each of the wires 116, 118 is connected to one of the connection terminals 112, 114 to allow selective biasing of the electrodes 50 of the controllably bendable portion 18.

The proximal end of the guidewire 12 is inserted into the housing 100 via the tapered inlet bore 102 whereby the guidewire 12 is grounded against the base 120 of the conduit 104. The first and second terminals 112, 114 are each configured as a strip of an electrically conductive material, such as copper, and 1 each includes a convex portion 122 overlying the slot opening 108. The first and second connection terminals 112, 114 are spaced from one another by distance 124 such that the center of the convex portions thereof are spaced from one another by the same distance as the distance between the centers of first and second terminals 80, 82. This allows for the movement of the proximal end of the guidewire 12 slightly outwardly and inwardly of the housing 100 without disconnecting the electrical circuit between the power source and the electrodes 50 on the electroactive polymer portion 34 of the controllably bendable portion 18. Likewise, the extension of the terminals circumferentially around the guidewire 12, the rotational orientation of the guide wire 12 does not impact the electrical circuit through the housing 100. The guidewire 12 may be fixed to the housing 100 such as by being press fit into the conduit 104 or a bonding agent may be applied between the base 120 of the conduit 104 and the guidewire 12. Alternatively, the guidewire 12 need not be fixed to the housing 100, and the guidewire 12 may be rotated therein without disrupting the contacting of the connection terminals 112, 114 with the terminals 80, 82.

Figure 11:
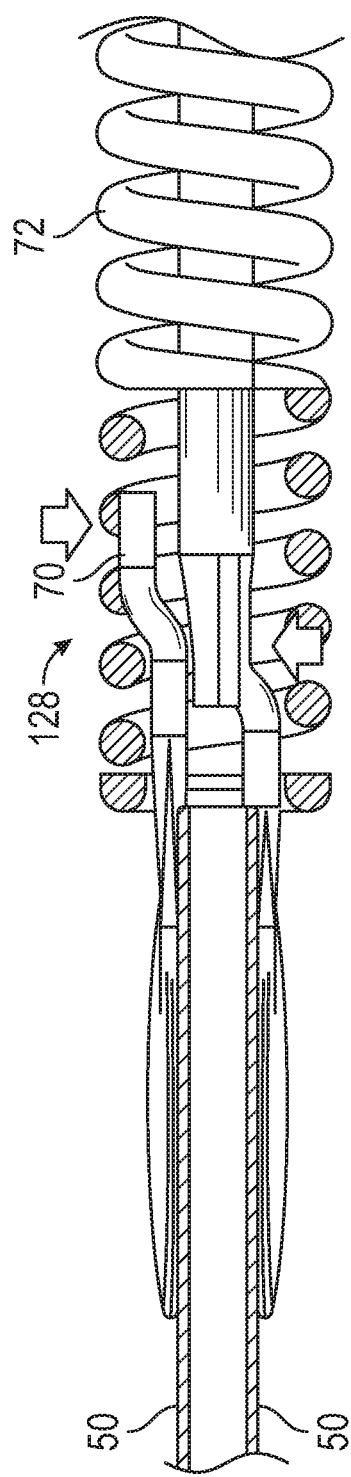
FIG. 11 is an enlarged side view, partially in section, of an alternate construct of connecting a power supply the controllably bendable tip end of the guidewire.
Figure 12:
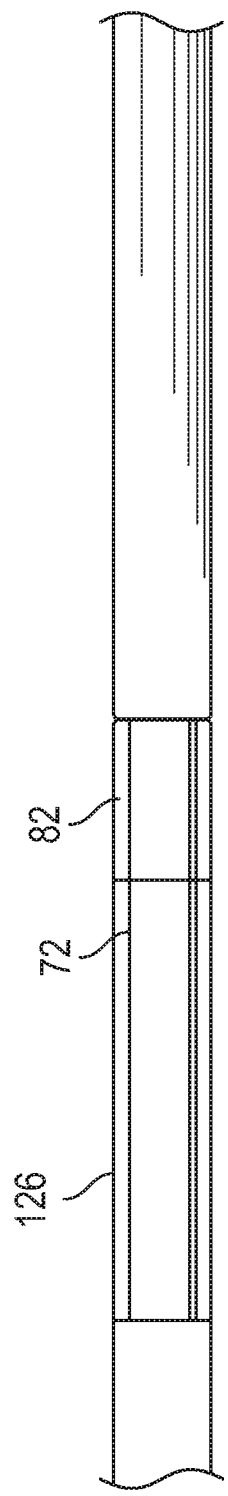
FIG. 12 is an enlarged side view of an alternate electrical connection portion of the guidewire.

Referring now to FIGS. 11 and 12, an alternate construct of the electrical connection paradigm to the electrodes 50 of the controllably bendable portion 18 is shown. Here, the wire 71 extends from the second terminal 82 at the intermediate portion 14 of the guidewire 12, and extends therethrough and through the intermediate portions 14, 16 (see FIG. 2) of the guidewire 12, and is connected to one of the electrodes 50 on the controllably bendable portion 18 in the same manner as shown in FIGS. 7 and 8. In contrast, the wire 70 is shortened as compared to its length in FIGS. 7 and 8, and it connects only between the first terminal 80 at the distal end of the electrical connection portion 16 and the other of the electrodes 50 of the controllably bendable portion 18. Here, intermediate portions 14, 16 are both configured of an electrically conductive material, for example stainless steel of other biocompatible electrically conductive portion. A portion 126 of the intermediate portion 14 serves as the second terminal. The end 128 of the wire 70 may be bent in dog leg fashion, such that it biases against the inner portion of the intermediate portion 14, 16 to allow a sliding electrical contact therebetween.

Figure 13:
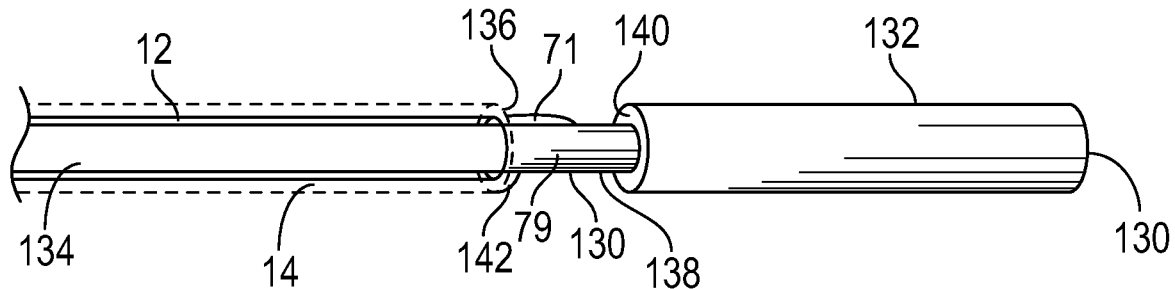
FIG. 13 is an enlarged isometric view of an alternate electrical connection portion of the guidewire with the terminal removed.
Figure 14:
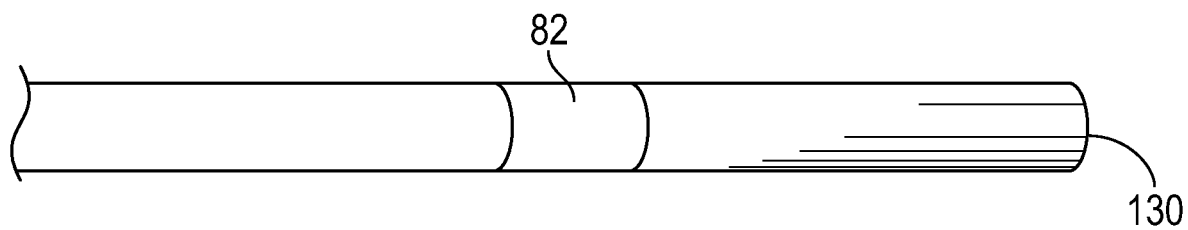
FIG. 14 is an enlarged isometric view of an alternate electrical connection portion of the guidewire.

Referring now to FIGS. 13 and 14, a connection paradigm to attach the wires 70, 71 to the terminals 80, 82, is shown, the connection paradigm being the same for each, but spaced along the length of the guidewire 12. Here, the proximal end of the tubular shaft 14 of the guidewire 12 includes an electrically insulative adaptor 130 including a minor diameter portion 134 partially extending therein, and a major diameter portion 132, wherein an annular ledge 140 formed between minor and major diameter portions 134, 132 is spaced from the end of the guidewire 12. The wire 71, including an insulator thereover, extends between the outer wall of the minor diameter portion 134 into a gap 138 formed between the annular end wall 136 of the guidewire 12 and the annular ledge 140. A portion of the insulation on the portion of the second wire 71 extending into the gap 138 is stripped or removed to expose the conductive core thereof. The terminal 82 is configured as a cylindrical conductor, and it is located in the gap 138. The annular end wall 136 includes an insulative coating thereon, or a separate insulating washer is disposed between the annular end wall of the conductive guidewire and the conductive terminal 80. The major diameter portion 132 is pressed or pushed in the direction of the guidewire 12 to secure the terminal, contacting the conductive core of the second wire 71 along its inner circumference, to complete the connection of the second wire 71 to the terminal as shown in FIG. 14. Although the connection paradigm has been described in terms of a single terminal, by proving a hollow adaptor 130 having a bore extending through the major and minor diameter portions thereof, drawing the second wire 71s therethrough, and inserting a second minor diameter portion of a second adaptor inwardly of the bore with the second terminal thereover, the second terminal 82 can be electrically connected to the conductive core of the second wire 71.

Figure 15:
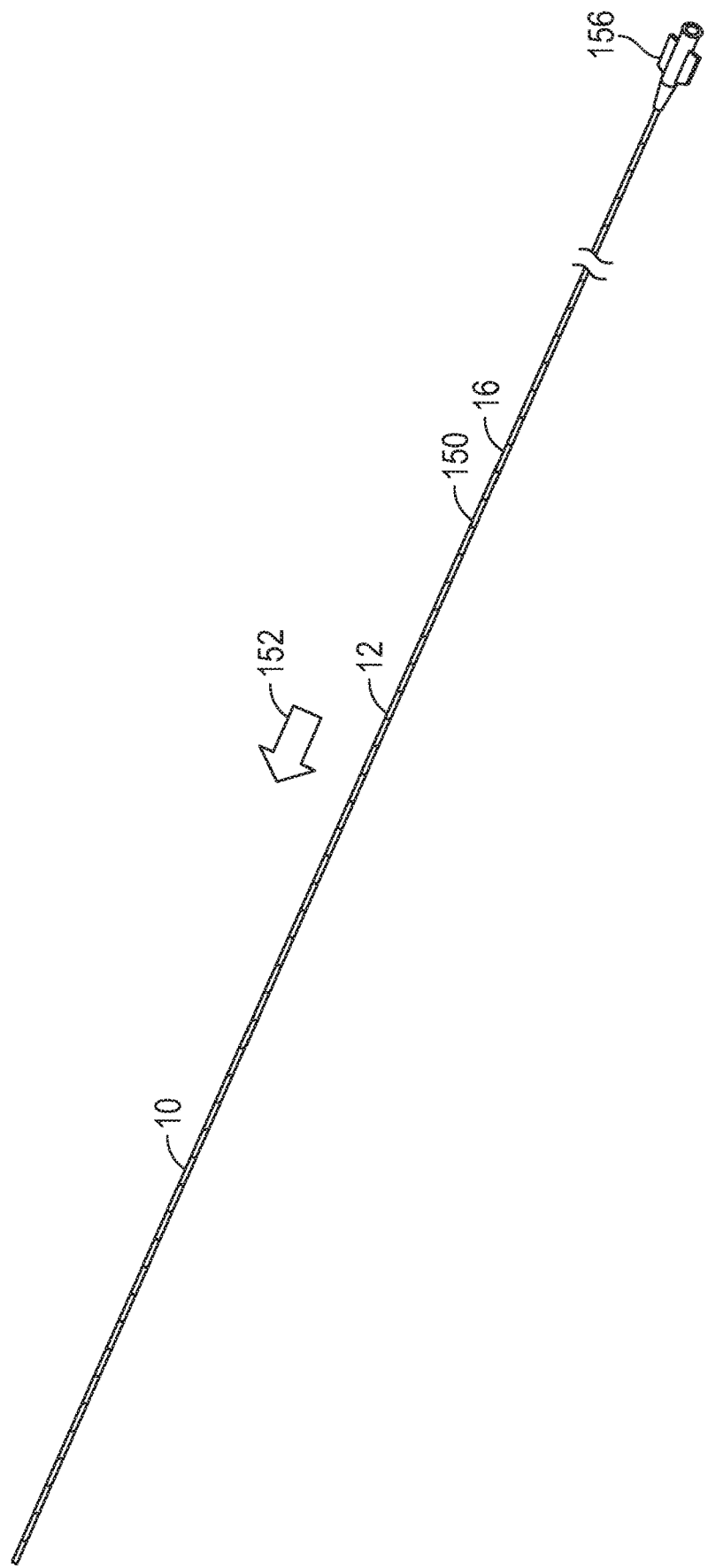
FIG. 15 is an isometric view of a step in the connection of the guidewire into the guide sheath.
Figure 16:
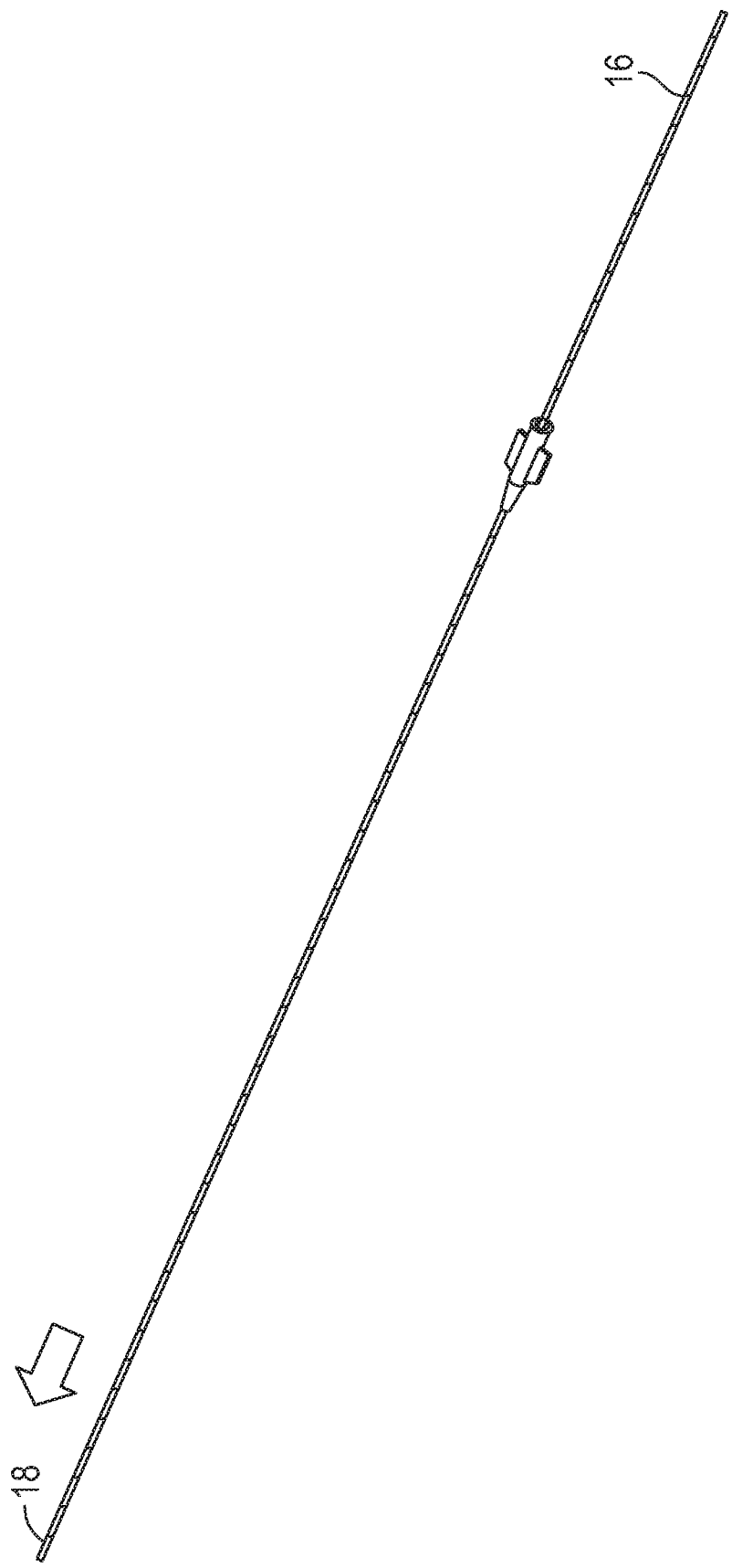
FIG. 16 is an isometric view of a step in the connection of the guidewire into the guide sheath.
Figure 17:
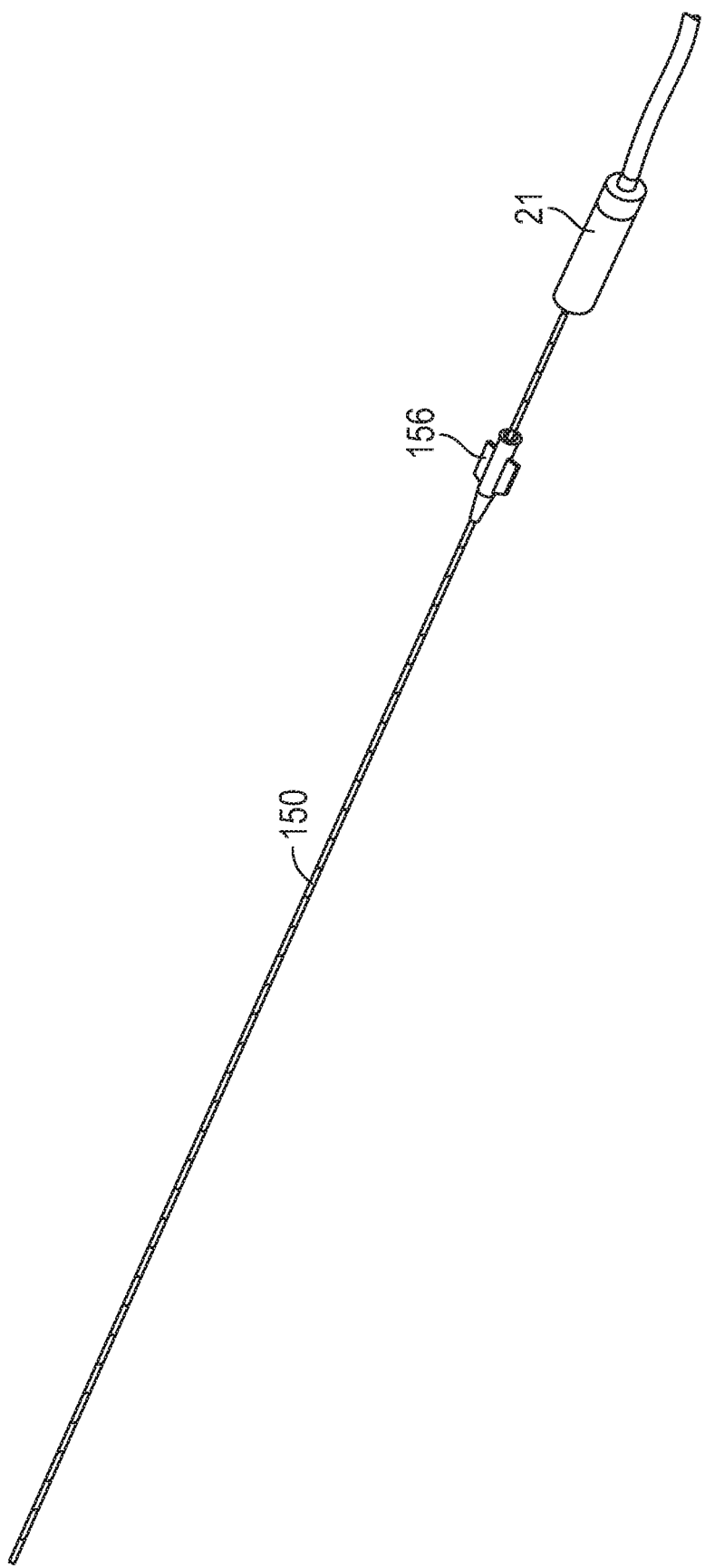
FIG. 17 is an isometric view of the guidewire and catheter, including the power supply connector, ready for use.

Referring now to FIGS. 15 to 17, the assembly of the guidewire system 10 with a guide tube 150 is shown. Initially, with the guidewire 12 is removed from the power supply connector 21 and the guide sheath is introduced over the guidewire from the intermediate portion 16 end thereof and pushed in the direction 152 to overlie the guidewire 12. The guide tube 150 includes a manipulator 156 at its proximal end thereof. The guide tube 150 and guidewire 12 are brought together such that the intermediate portion 16 extends outwardly of the guide tube 150 at the manipulator 156 end thereof, as shown in FIG. 16. Then, the intermediate portion 16 is inserted into the bore of the power supply connector 21.

Figure 18:
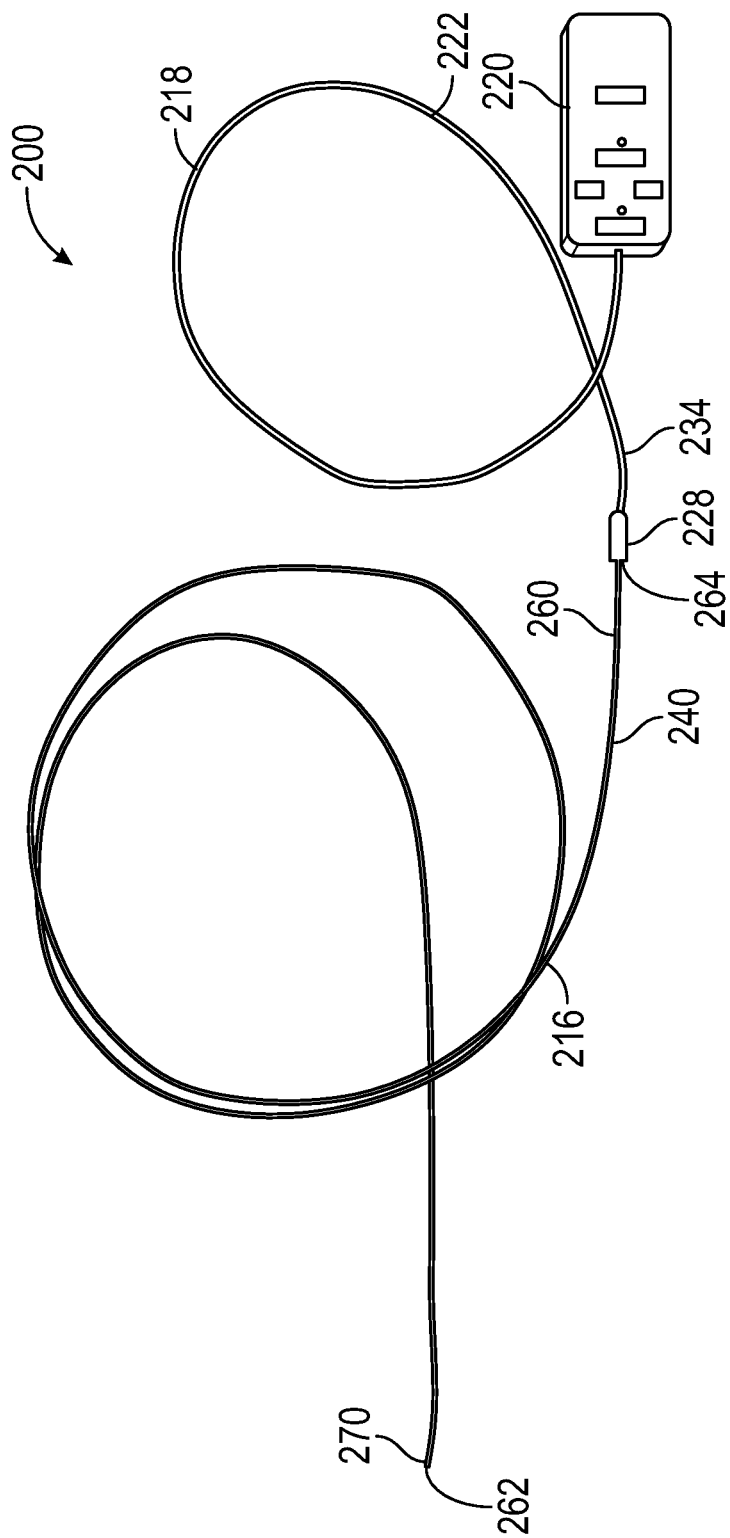
FIG. 18 is a schematic plan view of an additional aspect of a catheter including an outer sheath, and inner guidewire, and an electrical connection.
Figure 20:
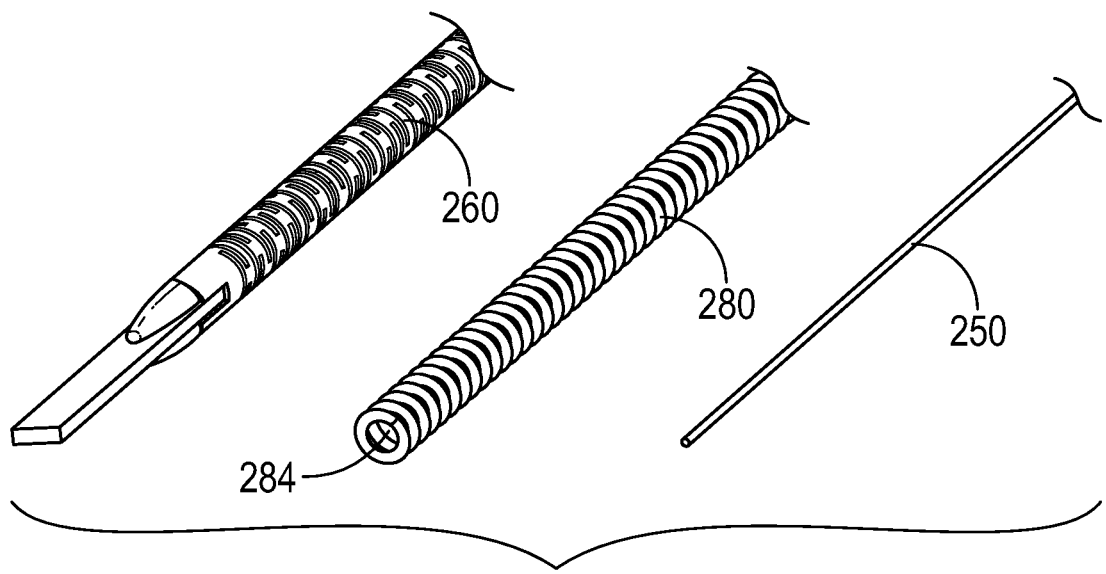
FIG. 20 is a sectional view of the outer sheath of the catheter of FIG. 18, showing the tapered core and other components disposed therein.
Figure 21:
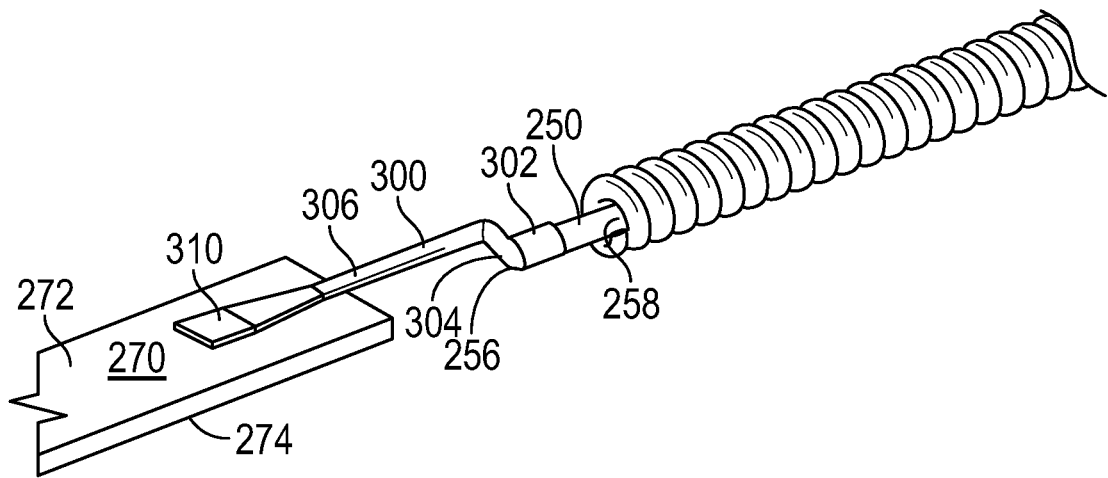
FIG. 21 is an isometric view of a conductive lead which extends from the tapered core to the electroactive polymer portion of the catheter of FIG. 18.

In this aspect of an introduction device, as shown in FIG. 18, an additional configuration of a guidewire and electroactive polymer based introduction device 200 includes a control and power module 218 including a power and control box 220, an electrical lead portion 222, having a flexible tubular protective covering 234 thereover and which extends from the control and power module 220 and terminates at a connection box 228, and a guidewire 216 which includes a hollow sheath 240 formed of an outer sheath formed as a hypotube 260 having a second end 264 receivable in the connection box 228 and a first end 262 distal thereto, the hypotube 260 selectively extending from the connection box 228 (see FIG. 20). The hypotube 260 includes therein, as shown in FIGS. 20 and 21, a core formed of a tapered core 250, and an electroactive polymer portion 270 extends from the first end 262 thereof. In this introduction device 200 configuration, a coil 280 is positioned over a portion of the tapered core 250 at a location thereof within the hypotube 260. The connection of the electroactive polymer portion 270 to a power source of the control and power module 218 occurs through the electrically conductive tapered core 250 and the hypotube 260, each of which is connected to separate conductors in the electrical lead portion 222 and the coil 280 provides a flexible support which, along with appropriate insulative coatings, electrically isolates the hypotube 260 and tapered core 250 from one another at the regions thereof immediately adjacent to the electroactive polymer portion 270 where significant bending of the hypotube 260 and guidewire 250 can be expected to occur. For example, the tapered core 250 is electrically connected to a first side 272 of the electroactive polymer portion 270, and the opposed second side 274 of the electroactive polymer portion 270 is electrically connected to the hypotube 260. For ease of introduction, the hypotube 260 may include a polymer sheath extending thereover, from the first end 262 to the second end 264 thereof.

Figure 19:
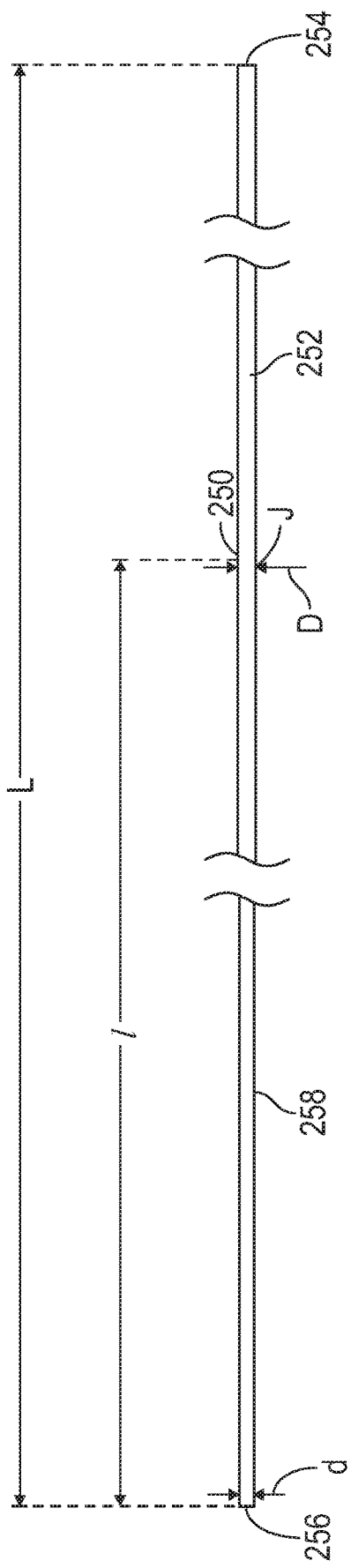
FIG. 19 is a plan view of a core or tapered core of the catheter of FIG. 18.

Referring to FIG. 19, the tapered core 250 is shown with portions thereof along its length removed. Tapered core 250 includes a main portion 252 extending from the first end 254 thereof and a tapered portion 258 extending from the second end 256 thereof in the direction of the first end 254. Here, approximately 15% of the length of the tapered core 250 is formed of the tapered portion 258 which extends contiguously from the main portion 252 at junction "J" wherein the smallest outer diameter d of the tapered portion 258 which is here occurring at second end 256 thereof is on the order of approximately 30% that of the outer diameter D of the main portion 258 along the length thereof. For example, where the total length "L" of the tapered core 250 is, for example, 200 cm (or two meters), the tapered portion 258 will extend a length "l" of 30 cm from the distal from the connection box 228 of the second end 256 thereof to the junction J of the tapered core 250. Additionally, where the diameter D of the main portion 252 is, for example, 0.20 mm, the tapered portion 258 tapers from the main portion 252 at the junction J to the distal, second end 256 thereof in a continuous, i.e., linear, reduction in outer diameter (D to d) over length "l" manner, such that the outer diameter "d" at the distal end 256 of the guidewire is on the order of 0.064 mm. Although the taper of the tapered portion 258 is described herein as occurring as a linear reduction of diameter over the length of the tapered portion 258, non-linear reductions in diameter along the length "l" from the main portion 252 to the distal end 256 are likewise contemplated. The tapering of the tapered portion 258 of the tapered core 250 adjacent to the distal end 256 thereof reduces the stiffness of the tapered core 250 thereat, and also creates a clearance space between the tapered portion 258 and the inner diameter of the hypotube 260 for receipt of the conductive coil 280 therebetween.

Figure 33:
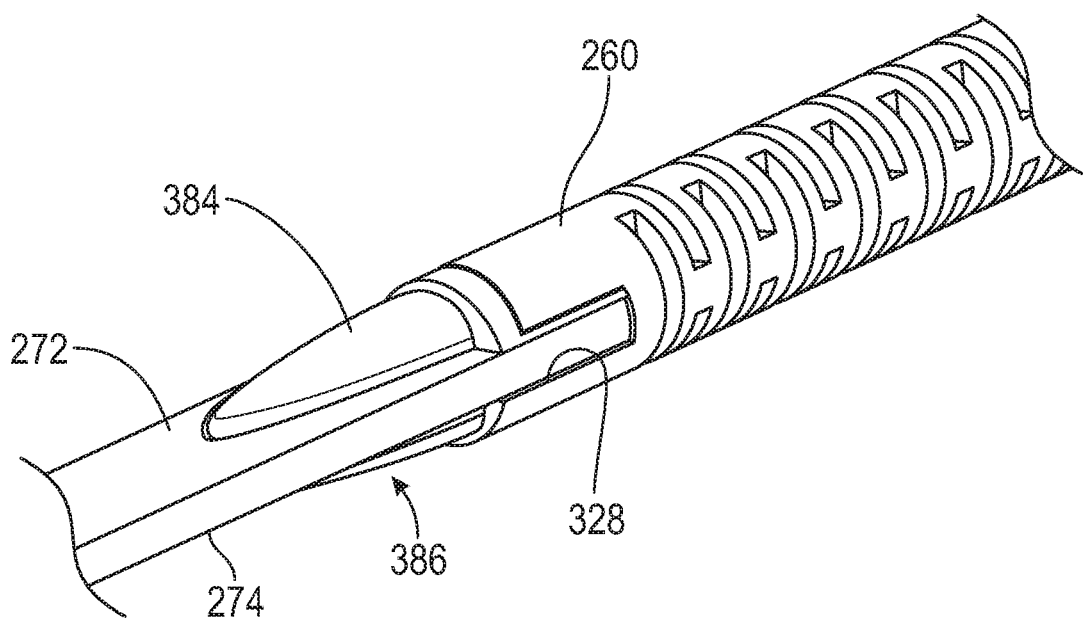
FIG. 33 is a view of the distal end of the outer sheath and the lead extending therefrom, with the electroactive polymer portion adhered into a slot in the outer sheath of FIG. 31 wherein the lead has been electrically connected to the first side of the electroactive polymer portion and the outer sheath has been electrically connected to the second side of the electroactive polymer portion.

Referring to FIG. 24A, the hypotube 260 is shown in section, showing the tapered core 250 extending within and along the inner circumference 284 of the hypotube 260, and the coil 280 extending around the portion of the tapered portion 258 of the tapered core 250 adjacent to the distal end 256 thereof and likewise within the inner circumference 284 of the hypotube 260. The hypotube 260 and tapered core 250 each provide a separate current path to support a voltage signal or current to be selectively placed or maintained on a thin electrode, such as a gold or silver layer, on the opposed first and second sides 272, 274 of the electroactive polymer portion 270. Here, a conductive lead 300 (FIG. 21) extends from the outer circumferential surface of the tapered portion 258 to connect to the first side 272 of the electroactive polymer portion 270). As shown on FIG. 21, the conductive lead 300 includes a first, generally flatted first portion 302, a dogleg portion 304 extending therefrom and away from the distal second end 256 of the tapered portion 258 of the tapered core 250, a lead portion 306 extending from the dogleg portion 304, and a second, generally flatted portion 310. The flatted first portion 302 is in electrical contact with the tapered portion 258 of the guidewire 250, such as by being spot welded thereto, and the second flatted portion 310 is connected to the first side 272 of the electroactive polymer member 270 such as by adhering them to one another with a first conductive layer 384 (FIG. 33).

Figure 22:
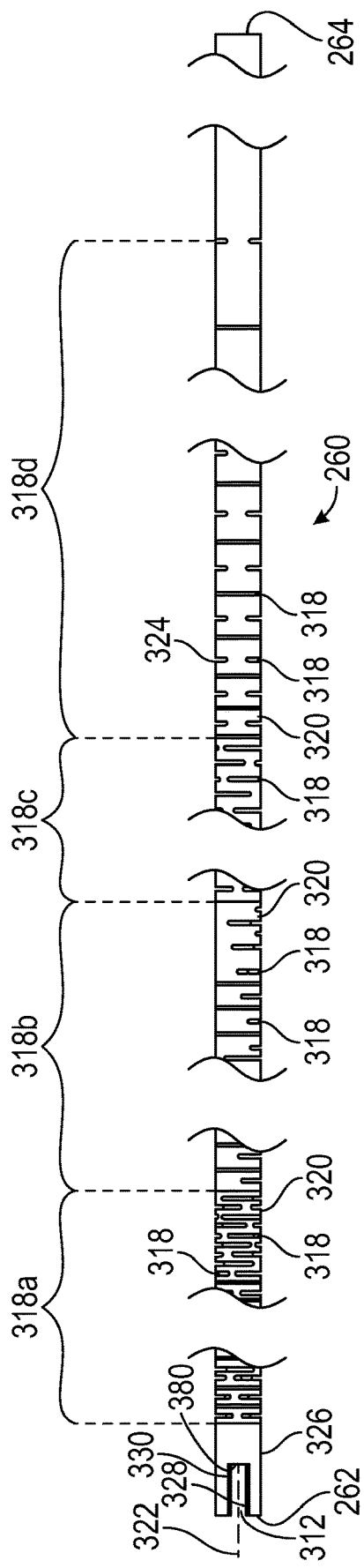
FIG. 22 is a plan view of the outer sheath of the catheter of FIG. 18.

The hypotube 260 here is a thin walled conductive sleeve s shown in FIG. 22, for example, a bio-compatible stainless steel tube, having a second tube end 264 receivable in the connection box 228, and a first tube end 262 configured with a receiving slot 312 having a slot height or width 314 slightly larger than the thickness 316 of the electroactive polymer portion 270 (FIG. 21). By configuring the width 314 of the receiving slot 312 slightly larger than the thickness 316 of the electroactive polymer portion 270, the first side 272 of the electroactive polymer portion 270 can be spaced from, and thus electrically isolated from, the inner wall of the receiving slot 312. The hypotube 260 further includes a plurality of cross cut slots 318 (see FIGS. 22 and 23) cut inwardly thereof from opposed circumferential sides thereof, to leave a pair of opposed webs 320 extending circumferentially between some of the pairs of slots. The cross cut slots 318 are formed only in a portion of the hypotube 260, that portion being adjacent to the first tube end 262 thereof and spaced slightly from the base of the receiving slot 312, and along the length of the hypotube 260 by a slightly greater distance than the length of the tapered portion 258 of the tapered core 250 disposed therein after assembly thereof, and the cross cut slots 318 are progressive, both in the size of the circumferential span of the webs 320, as well as the spacing of the cross cut slots 318 from one another. Here, the slots are laser cut into an otherwise continuous tube of material comprising the hypotube 260, but may be provided in other ways, such as physical cutting or milling, or pattern etching, or other mechanisms. Considering the hypotube 260 in an unbent or undistorted state as shown in FIG. 24 and having a centerline 322, each pair of cross cut slot 318 extend through the wall 324 of the hypotube 260 at an angle normal to (90 degrees to) the centerline 322, wherein the depth of the cut from the center of the circumferential span thereof forming each cross cut slot 318 defines the circumferential span of the cross cut slot 318 at the outer wall 324 of the hypotube 260, as well as the remaining circumferential span which comprises the webs 320 circumferentially extending between each end of each pair directly opposed of cross cut slots 318.

FIG. 22 depicts one such set of cross cut slots 318, wherein the slot frequency in the centerline 322 length direction of the hypotube 260 changes in relation to the distance along the hypotube 260 from the first tube end 262 thereof where the electroactive polymer portion 270 is received in the receiving slot 312. Here, four sets of slots 318a-d, each with different spacings from one another, different slot depths, or a combination of both, are present extending through the hypotube 260, wherein the deepest cross cut slots 318 are present in the first set of slots 318a adjacent to the first end 262 of the hypotube 260 and spaced from the receiving slot 312, and these cross cut slots 318 are likewise spaced closest to one another in the centerline 322 length direction of the hypotube 260. The cross cut slots 318 in the second set of slots 318 are disposed adjacent to the first set of slots 318a such that the first set of slots 318a is between the first end 262 of the hypotube 260 and the second set of slots 318b. The cross cut slots 318 in the second set of slots 318b are staggered in the centerline 322 length direction of the hypotube 260, such that cross cut slots 318 adjacent to one another circumferentially around the hypotube 260 are not formed on the circumferentially opposed sides of the hypotube at the same centerline 322 length location of the hypotube 260 from the first end 262 thereof. Rather, they are linearly staggered in the direction of the centerline 322 of the hypotube 260 by the same distance as the adjacent slots 318 in the centerline 322 length direction of the hypotube 260 in the first set of slots 318a. In the third set of slots 318c, the cross cut slots 318 are again opposed from each other circumferentially, and have a greater spacing from one another in the centerline 322 length direction of the hypotube 260 than those of the first or second sets of slots 318a, b, and the second set of slots 318b are disposed between the first set of slots 318a and the third set of slots 318c. The fourth set of slots 318d is disposed through the hypotube further distant of the first end 262 thereof than the location of the third set of slots 318c, and these include opposed pairs of cross cut slots 318, each of the pairs spaced progressively further from one another in the centerline 322 length direction of the hypotube 260 in the direction away from the second end 256 of the hypotube 260.

Figure 23:
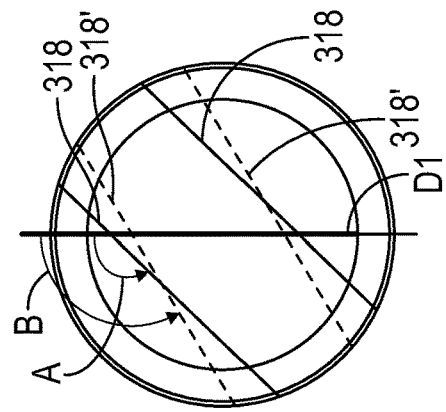
FIG. 23 is an schematic view of the outer sheath of FIG. 22, showing the relative angular difference between certain adjacent slots therein.

Additionally, in some of the sets of slots, the angular distribution thereof with respect to each other changes along the length direction of the hypotube. For example, FIG. 23 shows the angle of the sidewalls of two pairs of cross cut slots 318, 318' directly adjacent to one another in the length direction of the hypotube 260. Here, the base walls (solid lines) of the slots 318 extend at an angle A to reference direction D1, and the base walls (dashed lines) of the second set of slots 318' extend at angle B with respect to reference direction A, where the angle B is smaller than angle A. In the first second and third sets of slots 318a-c, each adjacent cross cut slot 318 is cut at a different angle to the reference direction, and the angular difference from one cross cut slot 318 to the next cross cut slot 318 in the length direction of the hypotube 260 is the same within each slot group 318a-c. This results in the orientation of the cross cut slots 318 precessing in the length direction of the hypotube, whereby the locations of the pivots formed by the webs 320 likewise precesses circumferentially around the hypotube 260 in the length direction thereof, allowing greater degree of flexibility of the hypotube 260. In this hypotube, the angular difference from cross cut slot 318 to cross cut slot 318' in the length direction of the hypotube in the first to third sets of slots is the same, and is on the order of 10 to 11.25 degrees. In each case, from cross cut slot 318 to cross cut slot, the direction of the angular change is the same direction. In the fourth set of slots 318d, each adjacent pair of cross cut slots 318 is offset from the adjacent pair of cross cut slots 318 by approximately 90 degrees. Additionally, where the spacing of the cross cut slots 318 of the first set of slots 318a is 0.0013 inches, the first cross cut slot 318 of the first set of slots 318a is spaced along the length of the tube 0.200 mm from the base of slot 312, slot 312 extends inwardly of the first end 262 of the hypotube 260 by 0.400 mm, and slot 312 is approximately 0.120 mm thick. The hypotube 260, for example, is configured of stainless steel, and has an outer circumference on the order of 0.0140 inches and an inner diameter on the order of 0.0100 inches.

As shown in FIGS. 20, 22 and 24B, in FIG. 24B a portion of the first set of slots 318a removed for clarity of the view, the hypotube 260 includes a continuous outer surface portion 326 extending between the base of the slot 312 and the closest cross cut slot 318 thereto. The second end 256 of the tapered core 250 is positioned inwardly of the hypotube 260 in the length direction thereof, and the conductive lead 300 extends therefrom to the first side 272 of the electroactive polymer portion 270. The slot 312 includes opposed first and second side walls 328, 330, and the hypotube 260 is electrically connected to the first side wall 328 by a conductive adhesive 332, or by other mechanism, and is electrically isolate from the second side wall 330 using a layer of insulating past or adhesive 334. Thus, the hypotube does not form a short circuit between the first and second sidewalls 328, 330 of the receiving slot 312 in the first end 262 of the hypotube 260 as shown in FIG. 22.

Figure 25:
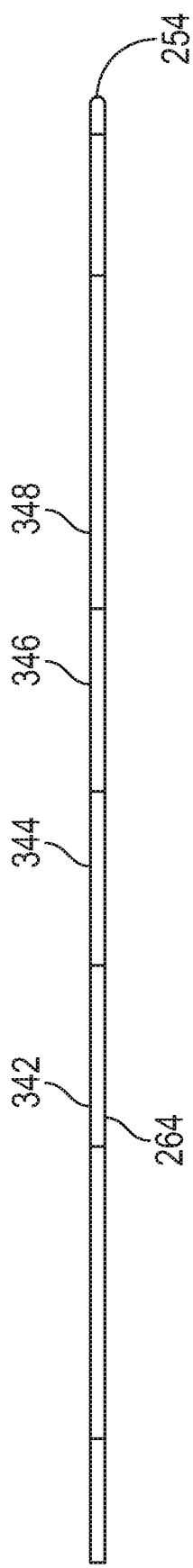
FIG. 25 is a plan view of the proximal end of the outer sheath, and inner guidewire, and an electrical connection components of the catheter of FIG. 18.
Figure 26:
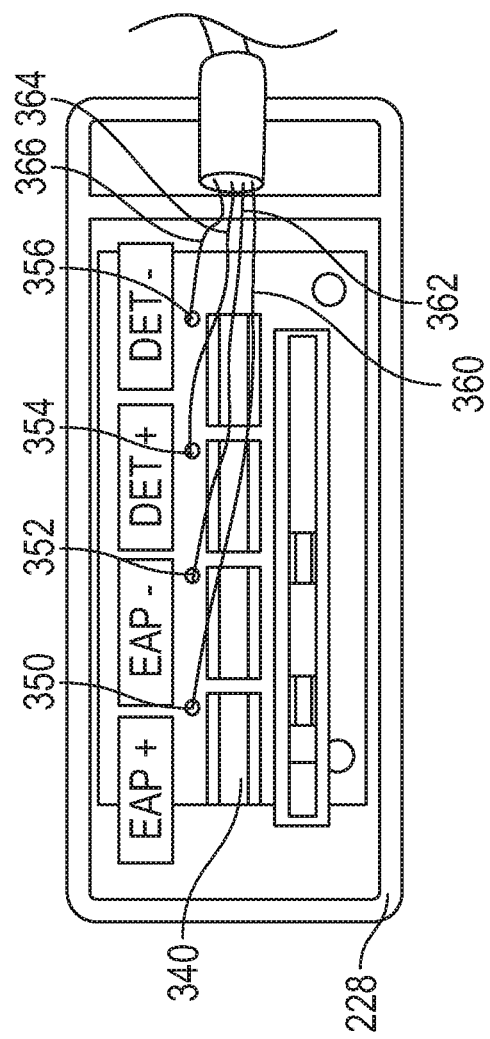
FIG. 26 is a plan view of the terminal arrangement of the control box of the catheter of FIG. 18.
Figure 27:
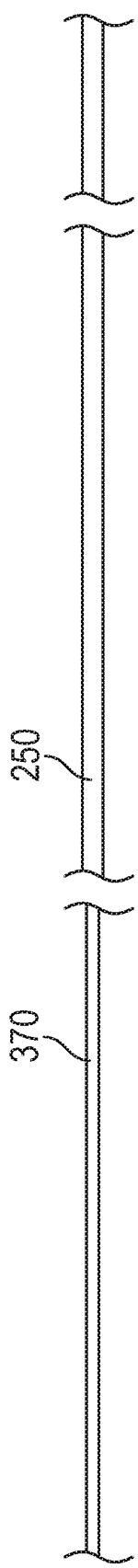
FIG. 27 is a plan view of the tapered core of the catheter of FIG. 18.

To connect the tapered core 250 and the hypotube 260 to different electrical sources, such as different output terminals of a single DC power supply, the first end 254 of the tapered core 250 extends outwardly of the second end 264 of the hypotube 260, and is receivable in an opening 340 in the connection box 228. Referring to FIG. 25, a first dielectric sleeve 342, a hollow connection band 344, a second dielectric sleeve 346 and a dummy electrode 348 extend, in that order and sequence, from the second end 264 of the hypotube 260. A portion of the main portion 252 of the tapered core 250 extends through the first dielectric sleeve 342, the hollow connection band 344, the second dielectric sleeve 346 and the dummy electrode 348. The tapered core 250 is electrically connected to the hollow connection band 344 by being electrically connected to the interior of hollow connection band 344, but is not in electrical connection with any of the first and second dielectric sleeves 342, 346 or the dummy electrode 348. The connection box includes a first terminal 350, a second terminal 352, a third terminal 354 and a fourth terminal 356, each of which are spaced from one another along the opening 340 in the connection box 228 and each of which includes a portion extending into the opening of the connection box 228. The distance between the portions of the first and second terminals 350, 352 extending inwardly of the opening 340 is at least as great as the length of the first dielectric sleeve 342, the distance between the portions of the second and third terminals 352, 354 extending inwardly of the opening 340 is at least as great as the length of the second dielectric sleeve 346, and distance between the portions of the third and fourth terminals 354, 356 extending inwardly of the opening is the difference 348. The first end 254 of the tapered core 250 extends outwardly of the dummy electrode 348, and sets the spacing between the end of the dummy electrode 348 and the base of the opening 340.

By inserting the dummy electrode 348, the second dielectric sleeve 346, the connection band 344, the first dielectric sleeve 342 and the portion of the hypotube 260 adjacent to the end 264 thereof, with the tapered core 250 extending therethrough, into the opening 340, and pushing them in until the end 254 of the tapered core 250 engages the base of the opening 240, the first terminal 350 will make electrical contact with the exterior of the hypotube 260, the second terminal 353 will make electrical contact to the hollow connection band 344, and thus to the tapered core 250 therein, and the third and fourth terminals 354, 356 will both make electrical contact with the dummy electrode 348. By passing a current into one of the third and fourth terminals 354, 356 from one terminal of a power supply (not shown), and connecting the other of the third and fourth terminals 354, 356 to the other terminal of the power supply, the current will flow though the dummy electrode 348 to indicate that the dummy electrode, and thus the hypotube 250 and guidewire 260 and hollow connection band 344 connected thereto are in proper placement within the connection box 228 to allow a voltage to be selectively placed on the first and second sides 272, 274 of the electroactive polymer portion through the tapered core 250 and hypotube 260, respectively. Four wires 360-366 extend into the connection box 228 from the control and power module 220 through the electrical lead portion 222. First wire 360 is connected to first terminal 350, and second wire 362 is connected to second terminal 352. For example, a positive voltage can be supplied through first wire 360 and a negative or a ground voltage supplied through second wire 362, to cause the electroactive polymer portion to bend in a first direction. Reversing those voltages will reverse the direction of bending. As previously described herein, the relative voltages supplied to the first and second sides 272, 274 of the electroactive polymer portion 270, both in polarity (+ or −) and magnitude, control the direction and extent of bending thereof. Third and fourth wires 364, 366 are connected to third and fourth terminals 354, 356 respectively, and the opposed ends thereof are connected to a different power supply (not shown) than that connected to first and second wires 360, 362, for example opposite poles (+, −) of a battery. When the third and fourth terminals 354, 356 make simultaneous contact with the dummy electrode 348, this completes an electrical circuit indicating that the connection box 228 is properly connected to the system, which can be indicated by the lighting of a led or other signaling element in the circuit.

Figure 29:
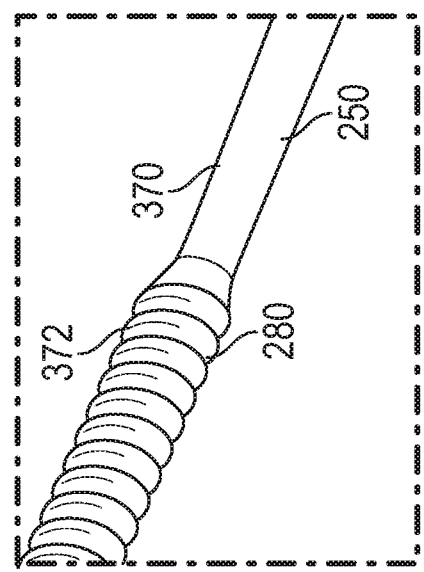
FIG. 29 is an isometric view of a second end of a coil bonded to the guidewire of FIG. 27.
Figure 28:
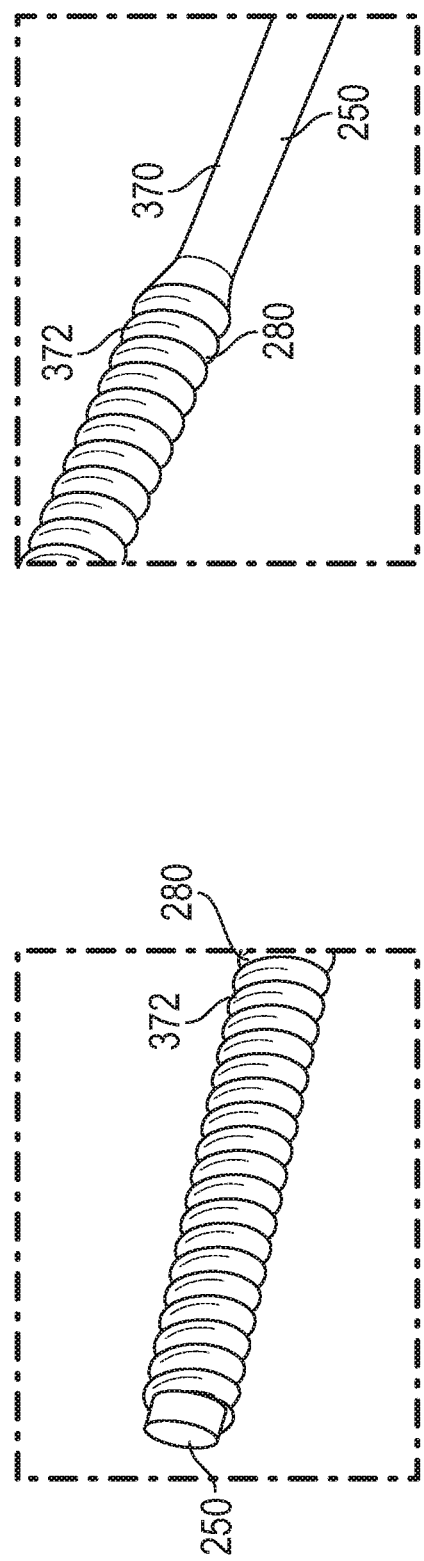
FIG. 28 is an isometric view of one end of a coil bonded to the guidewire of FIG. 27.

Referring now to FIGS. 27 to 34, portions of the manufacturing sequence of the introduction device 200 are shown. To prevent shorting between the tapered core 250 and the hypotube 260, the outer surface of the tapered core is covered with an insulating coating. For example, Parylene may be deposited on the tapered core 250 to form an insulative coating 370 (FIG. 27) thereon by vapor deposition using an adhesion promotor, the tapered core 250 may alternatively be dipped in an electrically insulative epoxy to form the insulative coating hereon, or other methods may be used to form the insulative coating. The coil 280 is then slid over the portion of the tapered portion 258 directly adjacent to the second end 256 of the tapered core 250, and secured thereto with a non-conductive adhesive 372, for example a non-conductive acrylic adhesive disposed between the inner diameter of the coil 260 and the outer circumference of the tapered portion 258, and over the coil 260, as shown in FIGS. 28 and 29. The first, generally flatted portion 302 of the lead 300 is then connected to the outer surface of the tapered core 250 at the second end 256 thereof, by locally removing the insulative coating 370 thereat and then welding or otherwise adhering them together, as shown in FIG. 21.

Figure 30:
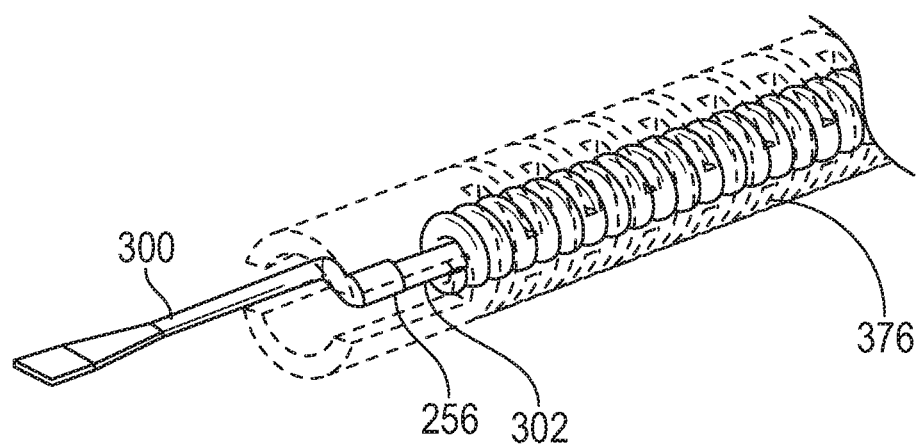
FIG. 30 is a view of the distal end of the outer sheath, and inner guidewire, and an electrical connection components showing the coil bonded to the interior of the outer sheath.

The first end 254 of the tapered core 250 having the lead 300 and coli 280 attached thereto, is then fed into the first end 262 of the hypotube 260, until the first end 254 of the tapered core 250 extends outwardly of the second end 264 of the hypotube 260 and the lead portion 306 extending from the dogleg portion 306, and the second, generally flatted portion 310 of the lead, extend outwardly of the first end 262 of the hypotube 260. A non-conductive adhesive is used to form a non-conducting bonding layer 376 between the non-conductive adhesive 372 and the inner surface of the hypotube 260 at least adjacent to the first end 262 of the hypotube 260 as shown in FIG. 30. This secures the locations of the tapered core 250 and hypotube 260 with respect to each other.

Figure 31:
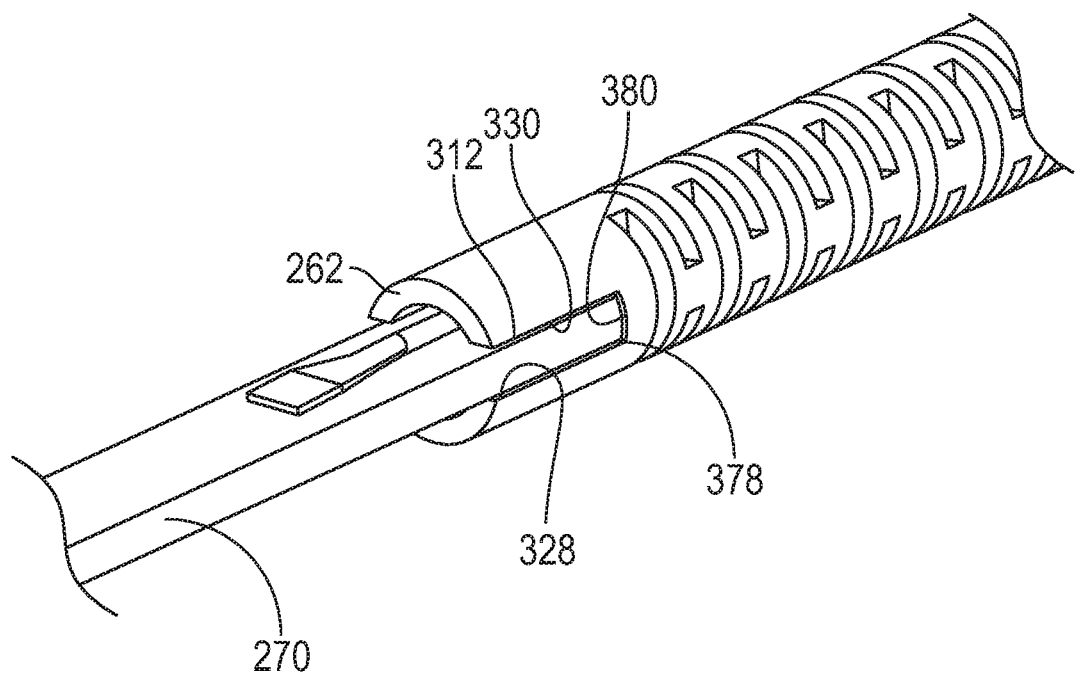
FIG. 31 is a view of the distal end of the outer sheath and the lead extending therefrom, with the electroactive polymer portion adhered into a slot in the outer sheath.
Figure 32:
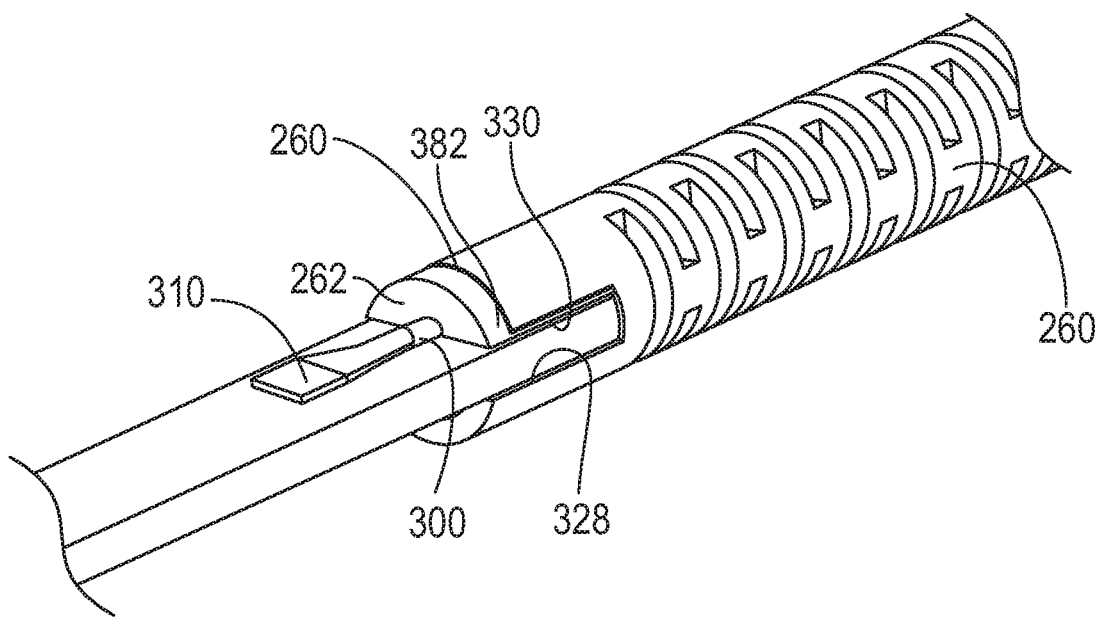
FIG. 32 is a view of the distal end of the outer sheath and the lead extending therefrom, with the electroactive polymer portion adhered into a slot in the outer sheath of FIG. 31, with an insulating material between the first side of the electroactive polymer portion and the outer sheath.

The fixing of the electroactive polymer portion 270 to the hypotube 260 is now performed. A coating of an adhesive 378 is disposed at the base 380 of the receiving slot 312, and the fixed end of the electroactive polymer portion 270 is inserted into the receiving slot 312 and contacted with the adhesive 378, such that a gap is present between the portion of the electroactive polymer in the receiving slot 312 and the opposed first and second side walls 328, 330 of the receiving slot 312 as shown in FIG. 31. The gap between the second side of the slot 312 and the electroactive polymer portion 270 is filled with an insulating filler 382, wherein the filler 382 extends over the first end of the hypotube 260, and the filler likewise covers the lead portion 306 of the lead 300 but leaves the second, generally flatted portion 310 exposed as shown in FIG. 32. Then the exposed second flatted portion 310 is covered by a first conductive layer 384 physically and electrically connecting the flatted portion 310 with the first side 272 of the electroactive polymer portion 270. A second conductive layer 386 is filled between the first side wall 328 of the receiving slot 312 and the second side 274 of the electroactive polymer portion 270 and extends along the second side 274 outwardly of the hypotube 260, to electrically connect the hypotube 260 with the second side 274 of the electroactive polymer portion, as shown in FIG. 33. First and second conductive layers 384, 386 are, for example, configured of a conductive paste, a conductive epoxy, or another conductive adhesive material.

Figure 34:
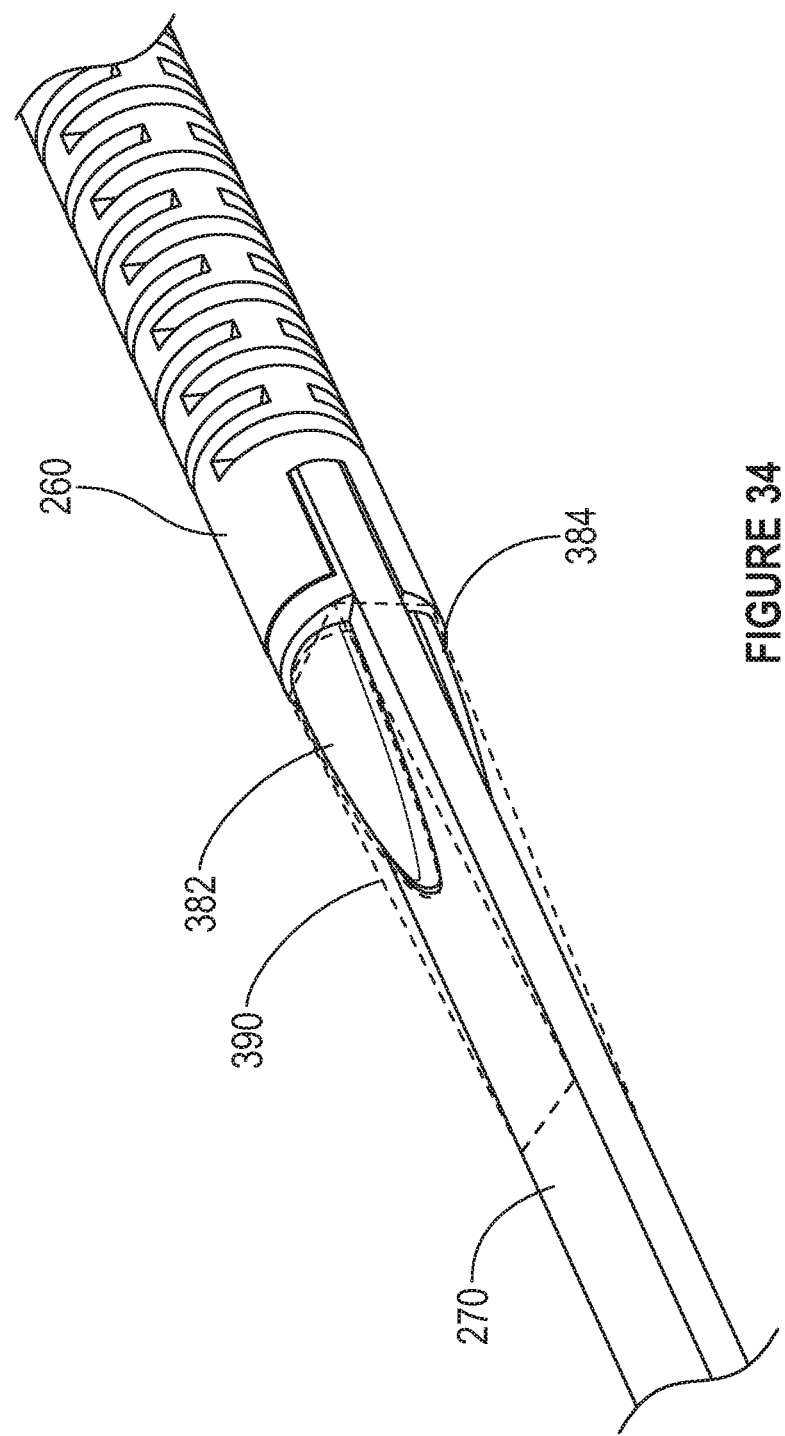
FIG. 34 is a view of the distal end of the outer sheath wherein the lead has been electrically connected to the first side of the electroactive polymer portion and the outer sheath has been electrically connected to the second side of the electroactive polymer portion and these portions are covered with an encapsulant.

Next, the hypotube 260 immediately adjacent to first end 262 thereof, and the first and second conductive layers 384, 386 and the immediately adjacent portions of the electroactive polymer portion 270 are covered in a thin layer of an encapsulant, such as silicone, followed by a coating of an adhesive agent such as parylene, followed by a second encapsulant, such as silicone (FIG. 34). The parylene is preferably vapor coated onto the relevant portions of the introduction device, whereas the silicone may be coated thereon by dip coating.

To use the introduction device, the first dielectric sleeve 342, the hollow connection band 344, the second dielectric sleeve 346 and the dummy electrode 346 are then slid over the portion of the tapered core 250 extending from the second end 264 of the hypotube 260, and secured thereto with adhesives. The first dielectric sleeve 342, the second dielectric sleeve 346 and the dummy electrode 346 are secured to the tapered core 250 using a non-conductive adhesive, and the hollow connection band 344 and the tapered core 250 are secured together with a conductive adhesive, or a press fit connection, to ensure electrical connection therebetween. The control box 220 is configured with push buttons, toggles, or other tactile elements by which an operator can, by movement or pressing of the tactile element, selectively apply voltages of desired polarity and magnitude to the first and second sides 272, 274 of the electroactive polymer portion to achieve the effects thereof shown with respect to the electroactive polymer portion of the bendable portion 18 of FIG. 2 hereof.

Referring now to FIGS. 35 to 49, there is shown an additional construct of a guidewire device, which uses the control and power module 218, the core configured as a tapered core 250 extending within the hypotube 260, the electroactive polymer portion 270 and other components of the device shown in, and described with respect to, FIGS. 18 to 24 hereof, wherein the electrical connection of the power source to the opposed first and second sides 272, 274 of the electroactive polymer portion is provided through dedicated conductors surrounded by an insulation, and thus the tapered core 250 and the hypotube 260 need not be electrically isolated from one another.

Figure 35:
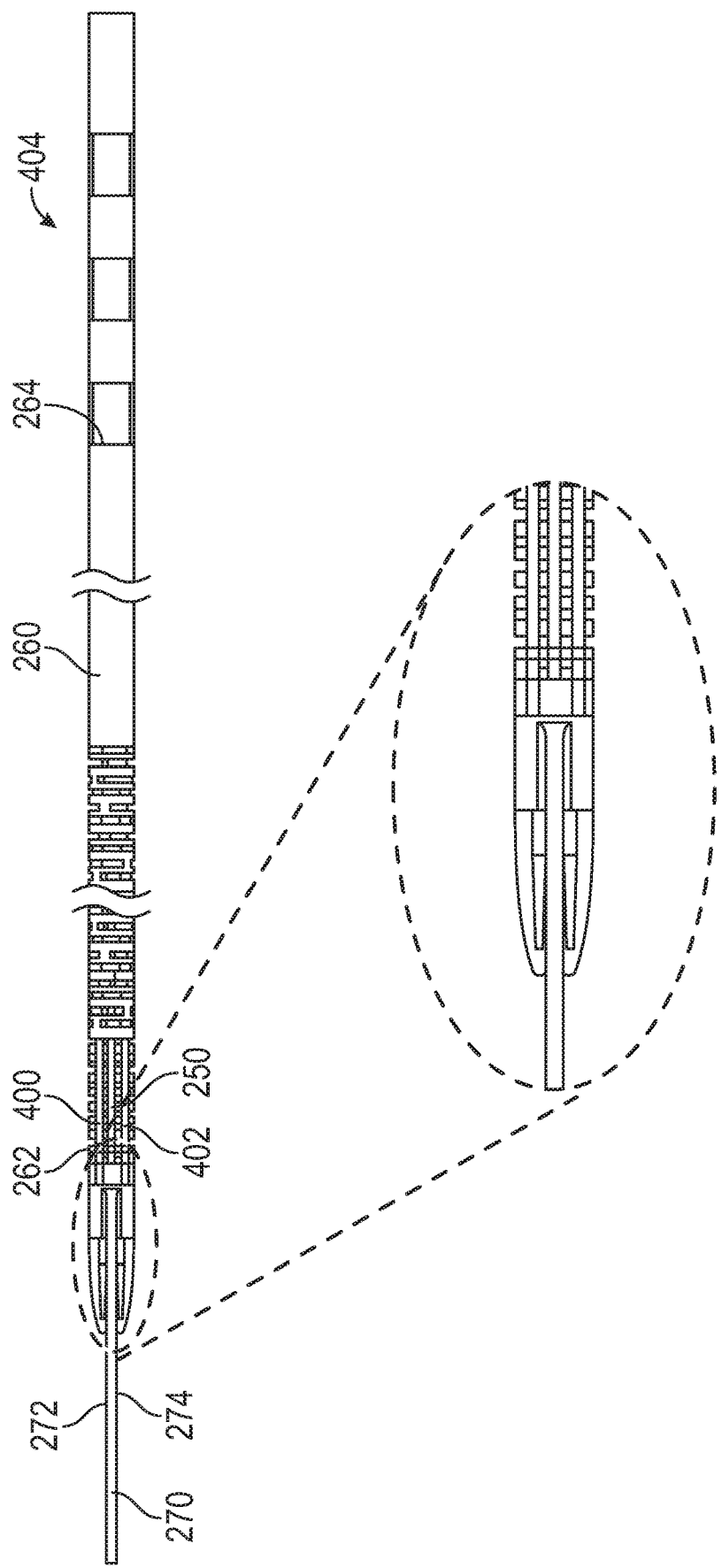
FIG. 35 is a plan view, partially in section, of an additional aspect of a guidewire.
Figure 39:
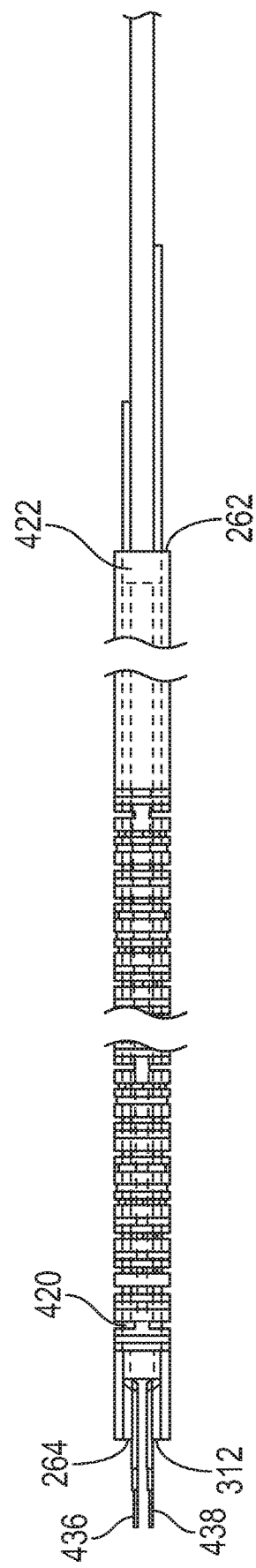
FIG. 39 is a plan view of a partially assembled guidewire of FIG. 35.

As shown in FIG. 35, wherein a portion of the hypotube 260 adjacent to the first end 262 thereof shown in section to reveal the details interior thereof, a first conductor 400 having a conductive core and a surrounding insulation, and a second conductor 402 having a conductive core and a surrounding insulation extend within the hypotube 260, wherein the conductive portion of the first conductor 400 is electrically connected to the first side 272 of the electroactive polymer portion 270, and the conductive portion of the second conductor 274 is connected to the second side 274 of the electroactive polymer portion 270. Here, the conductive portions of the conductors are configured of a base metal such as stainless steel and are covered with a thin layer of gold, but other conductive material coverings, such as silver, copper, cobalt or rhenium or ruthenium may be used as the conductor.

First and second conductors 400, 402 are electrically connected to the first and second sides 272, 274, respectively, of the electroactive polymer portion 270, with a conductive adhesive. Each conductor extends from its connection to the electroactive polymer portion, through the interior of the hypotube 260 and outwardly of the second end 264 of the hypotube 260 where they are connected to conductors of an electrical connection portion 404, which is receivable in the connection box 228 of the control and power module 218 as previously described herein.

The use of the conductors 400, 402 as the current carrying pathway to impose desired voltages on the first and second sides 272, 274 of the electroactive polymer portion 270 enables relatively simple assembly of the catheter or guidewire composed of the tapered core 250, hypotube 260, electroactive polymer portion 270, conductors 400, 402 and connection portion. To assembly the catheter or guidewire hereof, a fish 410 (FIG. 36), having the same diameter as the main portion 252 of the tapered core 240 is extended through the hypotube 260, such that the end 412 thereof extends outwardly of the first end of the hypotube 260. The conductors 400, 402 are placed over diametrically opposed sides of the tapered core adjacent to the first end 254 thereof, and a heat shrinkable tube 414 is extended thereover, such that the first end 254 of the tapered core 250 extends inwardly of a first open end 416 thereof, and the end 412 of the fish 410 extends inwardly of the second open end 418 thereof. Then, the heat shrinkable tube 414 is heated, causing it to contract radially and physically secure the conductors 400, 402, the fish 410 and the first end 254 of the tapered core together as shown in FIG. 37. Prior to this operation, the conductive portions of the conductors 400, 402 extending between the heat shrinkable tube 414 and the tapered core may be worked to flatten them to form a flat region similar to the flatted portion 302 of conductive lead 300, or a terminal (not shown) may be connected to each. These operations can also be performed once the conductors have been pulled through the hypotube 260 and exposed outwardly of the second end 264 thereof.

Figure 40:
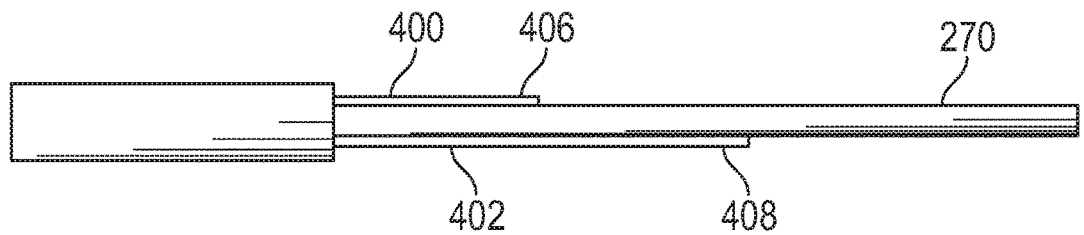
FIG. 40 is a plan view of the connection portion of a portion of the guidewire prior to the configuration of the electrical connection portion thereon.
Figure 41:
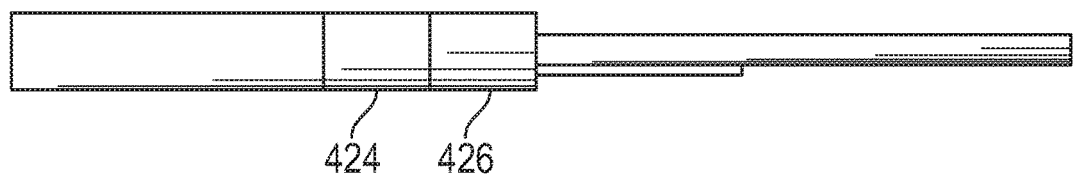
FIG. 41 is a plan view of the connection portion of a portion of the guidewire after a first portion of the electrical connection portion assembled thereon for electrical connection to a first conductor in contact with a first side of the electroactive polymer portion of the guidewire of FIG. 35.
Figure 42:
FIG. 42 is a plan view of the connection portion of a portion of the guidewire after a second portion of the electrical connection portion assembled thereon for electrical connection to a second conductor in contact with a second side of the electroactive polymer portion of the guidewire of FIG. 35.
Figure 43:
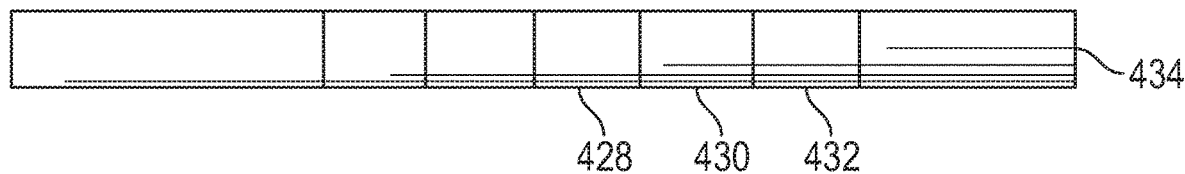
FIG. 43 is a plan view of the connection portion of the guidewire of FIG. 35 after a connection detector of the electrical connection portion is assembled thereon.
Figure 44:
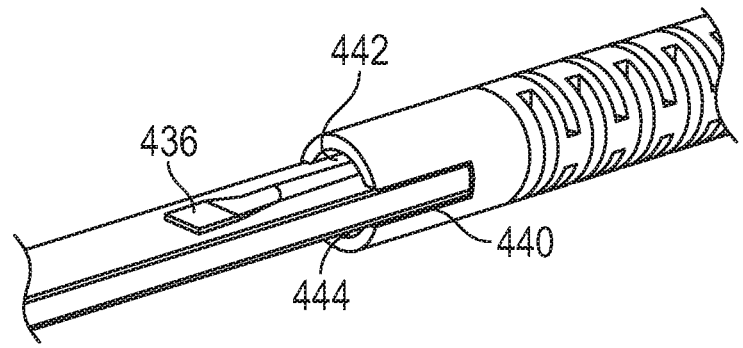
FIG. 44 is a partial isometric view of the distal end portion of a partially assembled guidewire of FIG. 35 showing the electroactive polymer portion connected to the outer sheath thereof.
Figure 45:
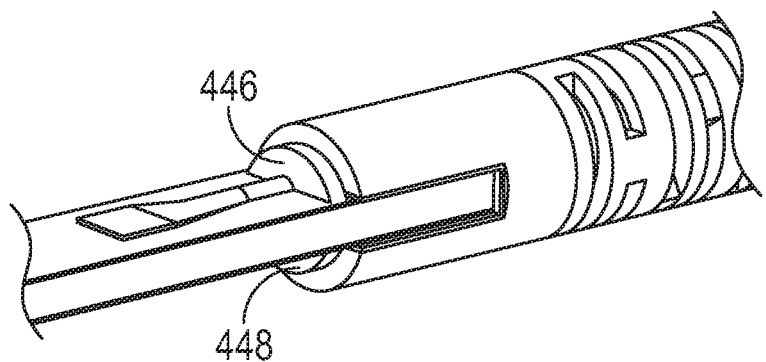
FIG. 45 is an additional partial isometric view of the distal end portion of a partially assembled guidewire of FIG. 35, showing the space between inner wall of the sheath and the electroactive polymer portion filled in, the filling further covering the adjacent end of the outer sheath.
Figure 46:
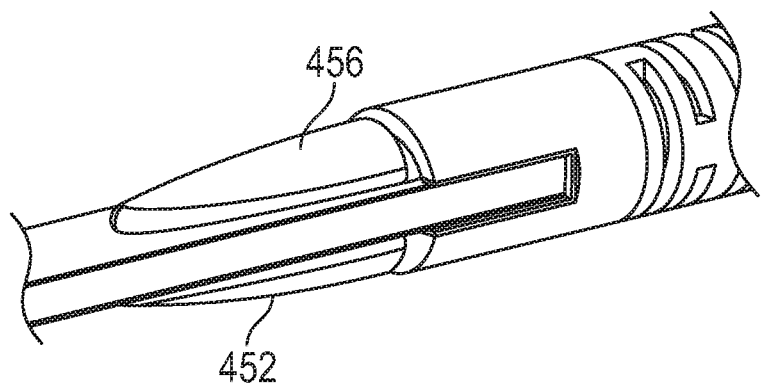
FIG. 46 is an additional partial isometric view of the distal end portion of a partially assembled guidewire of FIG. 35, showing a conductive adhesive covering the electrical connectors and the adjacent side of the electroactive polymer portion.
Figure 47:
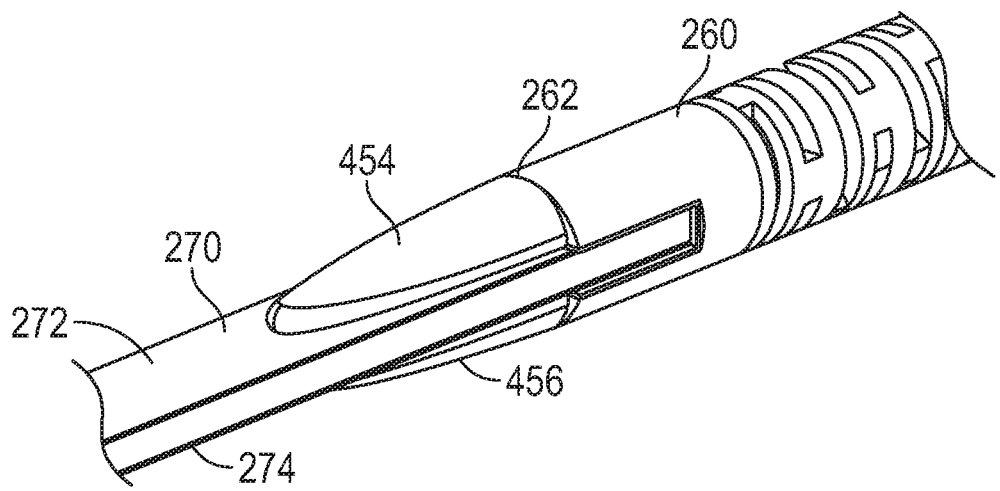
FIG. 47 is an additional partial isometric view of the distal end portion of guidewire of FIG. 35.

Then, the end 412 of the fish 410 is pulled in the direction of from the first end 262 toward the second end of the hypotube as shown in FIG. 38, until the heat shrinkable tube 410 is positioned outwardly of the second end 264 of the hypotube 260. Adhesive, such as an acrylic, is then injected into the opposed first end second ends 262, 264 of the hypotube 260, to form a first adhesion band 420 extending around the exterior of the tapered core 250 and the conductors 400, 402, and the interior of the hypotube 260 just inwardly of the second end 264 thereof and to form a second adhesion band 422 extending around the exterior of the tapered core 250 and the conductors 400, 402, and the interior of the hypotube 260 just inwardly of the first end 262 thereof. The conductors 400, 402 extend through the first adhesion band 420 and along the sidewalls of the receiving slot 312, The portion of the tapered core 250 extending outwardly of the second end 264 of the hypotube 260 is then covered with an insulative tube, which is heated to above its solidus temperature and allowed to reflow and adhere to the outer surface of the tapered core 250, and the conductors are disposable thereover. The electrical connection portion 404 is then formed by removing the insulative covering on the conductors 400, 402 at the ends 406, 408 thereof. (FIG. 40). Next, a first thin walled tubular insulator 424 is slid over the exposed portion of the tapered core 250, a conductive paste, such as a gold paste, is disposed interiorly of a first thin walled conductor 426, and the exposed conductive portion of first conductor 400 is connected thereto via the paste when the first thin walled conductor 426 is slid over the exposed portion of the tapered core 250 to abut the first thin walled tubular insulator 424. Thence a second thin walled tubular insulator 428 is slid over the exposed portion of the tapered core 250 to abut the first thin walled conductor 426, a conductive paste, such as a gold paste, is disposed interiorly of a second thin walled conductor 430, and the exposed conductive portion of second conductor 402 is connected thereto via the paste when the second thin walled conductor 430 is slid over the exposed portion of the tapered core 250 to abut the second thin walled tubular insulator 428. Then a third thin walled tubular insulator 432 is slid over the exposed portion of the tapered core 250, and a thin walled detection connector 434, which serves the same function as dummy electrode 348, is slid over the exposed portion of the tapered core 250 to abut the third thin walled tubular insulator 432 and adhered thereto with an adhesive. This completes the assembly of the electrical connection portion 404. The connection portion 404 is configured to be receivable into, and cooperatively operate in conjunction with, the connection box 228 previously described herein. When properly inserted into the opening in the connection box 228, first thin walled conductor 426 contacts the first terminal 350, second thin walled conductor 430 contacts the second terminal 352, and thin walled detection connector 434 contacts the third terminal 354 and the fourth terminal 356, each of which are spaced from one another along the opening 340 in the connection box 228 and each of which includes a portion extending into the opening of the connection box 228. Thus a voltage applied to the first terminal 350 is impressed on the first side 272 of the electroactive polymer portion 270, a voltage applied to the second terminal 352 is impressed on the second side 274 of the electroactive polymer portion 270, and a connection detection circuit is completed when the thin walled detection connector 434 contacts the third terminal 354 and the fourth terminal 356.

Figure 48:
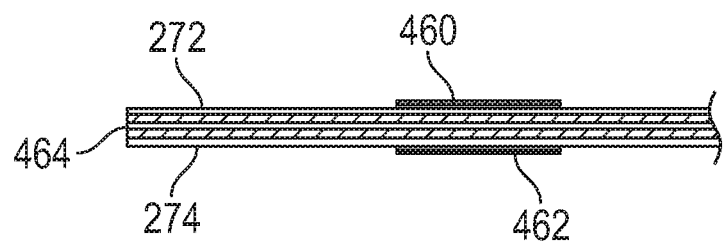
FIG. 48 is a schematic side view of a portion of the electroactive polymer portion hereof, showing a radiopaque marker on the opposed side surfaces thereof.
Figure 49:
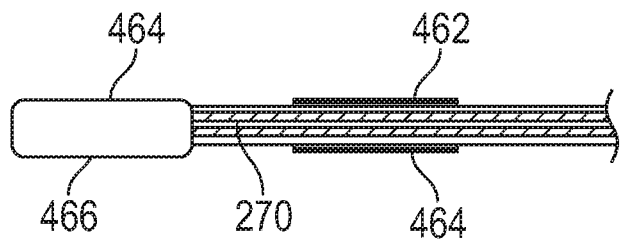
FIG. 49 is a schematic side view of a portion of the electroactive polymer portion of FIG. 48, showing a radiopaque marker on the tip end thereof.

The electroactive polymer portion 270 is secured within receiving slot 312 by inserting one end thereof into the receiving slot 312, where the first and second sidewalls 328, 330 and base of the receiving slot 314 have been covered with an adhesive, such as an acrylic adhesive, to contact the adhesive which upon curing forms a securing layer 440, When the end of the electroactive polymer portion 270 is inserted into the receiving slot 312, the flattened terminal ends 436, 438 thereof (FIG. 44) are located over the opposed first and second sides 272, 274 of the electroactive polymer portion 270. Next, the open regions 442, 444 between the portions of the first and second sides 727, 274 of the electroactive polymer portion 270 and the inner wall of the hypotube 260 (FIG. 44), are filled with an adhesive to form plugs 446, 448. (FIG. 45) Plugs may be formed of, for example, an acrylic adhesive which when cured forms the plugs 446, 448. Next, the flatted terminal portions 436, 438 are electrically connected and secured to the first and second sides 272, 274, respectively, of the electroactive polymer portion with a conductive slug 456, 452. Conductive slug may comprise, for example, a cured conductive epoxy, for example a gold filled epoxy. (FIG. 46) Then the exposed portion of first end 262 of the hypotube 260, and the slugs 456, 452, as well as adjacent portions of the first and second sides 272, 274 of the electroactive polymer portion 270 are covered with a layer of encapsulant 454, 456 respectively, composed of, for example, a silicone adhesive. Next, radiopaque marker plates 460, 462 are attached to the opposed first and second sides 272, 274 of the electroactive polymer portion 270 as shown in FIG. 48. The marker plates 460, 462 are, for example, composed of a platinum iridium alloy and are disposed slightly inwardly of the tip end 464 of the electroactive polymer portion 270 on the opposed first and second sides 272, 274 thereof. Each marker plate 460, 462 is disposed less than one millimeter from the tip end 464 of the electroactive polymer portion 270, and each is less than one mm in length. For example one-half of a millimeter in length. Alternatively, the tip end 464 of the electroactive polymer portion 272 may be coated with a radiopaque layer 466, for example the platinum iridium alloy or a gold layer, in addition to, or as an alternative to, marker plates 462, 464. Thereafter, the electroactive polymer portion 272, the encapsulant 454, 456, and the adjacent portion of the hypotube 260 are dipped into a silicone dispersion to be coated therewith, and then the hypotube 260, and the dip coated electroactive polymer and encapsulant 452, 454 extending therefrom, are vapor coated with a coating of, for example, parylene. The vapor coated electroactive polymer portion 272, the encapsulant 454, 456, and the adjacent portion of the hypotube 460 are dipped into a silicone dispersion to be coated therewith, the hypotube 260, and the dip coated electroactive polymer and encapsulant 452, 454 are again coated with a vapor coating of, for example, parylene, and then the parylene coating is covered with a hydrophilic coating to complete the assembly of the catheter or guidewire portion of the system.

What is claimed is:

1. A catheter comprising:
    a hollow sheath;
    a guidewire extendable through the hollow sheath, the guidewire comprising:
    a controllably bendable distal portion;
    a hollow tubular intermediate portion connected to the distal portion;
    a proximal electrical connection portion connected to the hollow tubular portion;
    at least a core extending through the hollow tubular portion and connected at a proximal end thereof to the proximal electrical connection portion and at a distal end thereof to a surface of a tip end of the distal portion; and
    a power supply connector, wherein the electrical connection portion is received in the power supply connector and a first terminal in the power supply connector contacts the proximal electrical connection portion;
    wherein the controllably bendable distal portion comprises:
    an electroactive polymer core having opposed first and second faces;
    a first carbon layer formed on the first face and a second carbon layer formed on the second face.

2. The catheter of claim 1, further comprising:
    a first electrically-conductive wire extending respectively through the hollow tubular portion and connected at a proximal end thereof to a first circumferential connector and at a distal end thereof to a surface of the tip end other than the surface to which the core is connected
    a second electrically-conductive wire extending respectively through the hollow tubular portion and connected at a proximal end thereof to a second circumferential connector and at a distal end thereof to a surface of the tip end other than the surface to which the core and the first wire are connected; and
    wherein the first terminal in the power supply connector contacts the second circumferential connector.

3. The catheter of claim 1, wherein the tip end of the guidewire is pre-bent.

4. The catheter of claim 1, wherein the thicknesses of the first and second carbon layers are different.

5. The catheter of claim 1, further comprising a first metal layer on the first carbon layer and a second metal layer on the second carbon layer.

6. The catheter of claim 1, wherein the hollow tubular intermediate portion is served as a first conductor, while the core is served as a second conductor.

7. The catheter of claim 1, wherein the hollow tubular intermediate portion further comprises a patterned laser cut surrounding an outer surface thereof.

8. The catheter of claim 1, wherein the core further comprises a coil tube surrounding at least a portion of the distal end thereof.

9. The catheter of claim 1, wherein the core further comprises a tapered portion at the distal end thereof.

10. The catheter of claim 1, wherein the proximal electrical connection portion further comprises a first circumferential conductor and a second circumferential conductor.

11. A guidewire comprising:
    a controllably bendable distal portion;
    a hollow tubular intermediate portion connected to the distal portion;
    a proximal electrical connection portion connected to the hollow tubular portion;
    at least a core extending through the hollow tubular portion and connected at a proximal end thereof to the proximal electrical connection portion and at a distal end thereof to a surface of a tip end of the distal portion; and
    a power supply connector, wherein the electrical connection portion is received in the power supply connector and a first terminal in the power supply connector contacts the proximal electrical connection portion
    wherein the controllably bendable distal portion comprises:
    an electroactive polymer core having opposed first and second faces;
    a first carbon layer formed on the first face and a second carbon layer formed on the second face.

12. The guidewire of claim 11, wherein the hollow tubular intermediate portion is served as a first conductor, while the core is served as a second conductor.

13. The guidewire of claim 11, wherein the hollow tubular intermediate portion further comprises a patterned laser cut surrounding an outer surface thereof.

14. The guidewire of claim 11, wherein the core further comprises a coil tube surrounding at least a portion of the distal end thereof.

15. The guidewire of claim 11, wherein the core further comprises a tapered portion at the distal end thereof.

16. The guidewire of claim 11, wherein the proximal electrical connection portion further comprises a first circumferential conductor and a second circumferential conductor.

17. The guidewire of claim 16, further comprising:
    a second electrically-conductive wire extending respectively through the hollow tubular portion and connected at a proximal end thereof to a second circumferential connector and at a distal end thereof to a surface of the tip end other than the surface to which the core and the first wire are connected; and
    a power supply connector, wherein the electrical connection portion is received in the power supply connector and a first terminal in the power supply connector contacts the first circumferential conductor and the second circumferential connector.

18. The guidewire of claim 11, wherein the tip end of the guidewire is pre-bent.

19. The guidewire of claim 11, wherein the thicknesses of the first and second carbon layers are different.

20. The guidewire of claim 11, further comprising a first metal layer on the first carbon layer and a second metal layer on the second carbon layer.

\* \* \* \* \*